(12) United States Patent
Kiyota

(10) Patent No.: US 8,541,228 B2
(45) Date of Patent: Sep. 24, 2013

(54) CELL OBSERVATION APPARATUS, CELL OBSERVATION METHOD, AND PROGRAM

(75) Inventor: Yasujiro Kiyota, Tokyo (JP)

(73) Assignee: Nikon Corporation, Tokyo (JP)

(*) Notice: Subject to any disclaimer, the term of this patent is extended or adjusted under 35 U.S.C. 154(b) by 724 days.

(21) Appl. No.: 12/451,384

(22) PCT Filed: Jun. 20, 2008

(86) PCT No.: PCT/JP2008/061297
§ 371 (c)(1),
(2), (4) Date: Nov. 10, 2009

(87) PCT Pub. No.: WO2009/001759
PCT Pub. Date: Dec. 31, 2008

(65) Prior Publication Data
US 2010/0129849 A1    May 27, 2010

(30) Foreign Application Priority Data
Jun. 22, 2007 (JP) ................. 2007-165269

(51) Int. Cl.
*C12M 1/00* (2006.01)

(52) U.S. Cl.
USPC ................... 435/303.1; 435/287.1

(58) Field of Classification Search
USPC ..................................... 435/287.1
See application file for complete search history.

(56) References Cited

FOREIGN PATENT DOCUMENTS

| JP | A-61-023003 | 1/1986 |
|---|---|---|
| JP | A63-262754 | 10/1988 |
| JP | H6-4542 | 1/1994 |
| JP | A-07-225796 | 8/1995 |
| JP | A-2002-277754 | 9/2002 |
| JP | A-2004-102469 | 4/2004 |
| JP | A-2007-006852 | 1/2007 |
| JP | A-2007-129971 | 5/2007 |
| JP | A-2008-139579 | 6/2008 |
| WO | WO 2007/055317 A1 | 5/2007 |

OTHER PUBLICATIONS

Czirok et al. "Multi-field 3D scanning light microscopy of early embryohenesis", J of Microscopy, 2002, 206(Pt.3):209-217.*
LeSage et al. "Design and implementation of algorithms for focus automation in digital imaging time-lapse microscopy", Cytometry, 2002, 49:159-169.*
Collazo et al.., "Use of confocal microscopy in comparative studies of vertebrate morphology," Methods Enzymology, 2005, vol. 395, pp. 521-543.
International Search Report issued in PCT/JP2008/061297 on Sep. 12, 2008.
Mar. 26, 2013 Office Action issued in Japanese Patent Application No. 2009-520546 (translation).

* cited by examiner

*Primary Examiner* — Bin Shen
(74) *Attorney, Agent, or Firm* — Oliff & Berridge, PLC

(57) ABSTRACT

The present invention relates to a cell observation apparatus that facilitates the setting of schedules. An observation schedule that has already been registered is presented to a user by a time schedule display unit of a schedule setting screen, and a new observation schedule is acquired in response to an input of set values of photographic conditions by the user. Then determination is made whether the photographing time of this observation schedule and the photographing time of the already registered observation schedule overlap, and when the photographing times are determined to overlap, the photographic conditions including the photographing time of one or both of the observation schedules are changed and the observation schedule is registered. The invention can be applied, for example, to incubators for culturing cells.

8 Claims, 15 Drawing Sheets

FIG. 7

| SET VALUE INPUT OF PHOTOGRAPHIC CONDITIONS OF NEW SCHEDULE |
|---|

PHOTOGRAPHING INTERVAL — 162  ALLOWED TIME

2 ∧ HOURS    00 ∧ MINUTES    15 ∨
3                10                          ⤴ 166
  ∨ — 161       20              MINUTES
PHOTOGRAPHING TIME  30 ≡
20 ∨ MINUTES   40
        ↖ 163          50
                              60 ∨

PHOTOGRAPHING START TIME   ⤴ 164
YEAR    MONTH   DAY    HOURS   MINUTES
2007 ∨   4 ∨   10 ∨    00 ∨    00 ∨

PHOTOGRAPHING END TIME   ⤴ 165
YEAR    MONTH   DAY    HOURS   MINUTES
2007 ∨   4 ∨   11 ∨    09 ∨    00 ∨

160

CELL OBSERVATION APPARATUS, CELL OBSERVATION METHOD, AND PROGRAM

This is a national stage application of PCT/JP2008/061297, filed on Jun. 20, 2008, which claims the benefit of JP 2007-165269, filed on Jun. 22, 2007. The disclosure of the prior applications is hereby incorporated by reference herein in its entirety.

BACKGROUND OF THE INVENTION

1. Field of the Invention

The present invention relates to a cell observation apparatus, a cell observation method, and a program, and more particularly to a cell observation apparatus, a cell observation method, and a program that can facilitate the setting of schedules.

2. Description of the Related Art

In a cell (culture) observation apparatus that serves to observe the culturing process of cells, the cells are cultured in a culturing atmosphere maintained under conditions suitable for cell culturing. Further, in the cell observation apparatus, time lapse photography is performed to photograph the cells at predetermined intervals in order to confirm that the cells are cultured normally. The user observes the state of the cultured cells on the basis of images obtained with the time lapse photography.

For example, Japanese Patent Application Laid-open No. 2002-277754 discloses a microphotographic apparatus that can perform time lapse photography in a plurality of photographic ranges, without limitations placed by the observation field of the microscope.

In the conventional cell observation apparatus, the user sets a photographic magnification for photographing the cells, a Z stack number, and a number of photographic points, determines the photographing time on the basis of these settings, and sets the photographic conditions such as the photographing frequency and photographing interval for time lapse photography by the photographing time, and the time lapse photography is performed according to a schedule based on the photographic conditions. However, in a case where the schedule that is newly registered by the user overlaps the already registered schedule, time lapse photography sometimes cannot be performed according to the schedule. Thus, in the conventional cell observation apparatus, whether or not the photographic conditions are adequate is not determined when the user registers a schedule.

Therefore, the user has to be careful to avoid overlapping with the already registered schedule or has to adjust the settings such as the photographic magnification, stack number, and number of photographic points by conducting preliminary tests to determine the photographic conditions, and schedule setting cannot be easily performed.

SUMMARY OF THE INVENTION

With the foregoing in view, it is an object of the present invention to facilitate the setting of schedules.

A cell observation apparatus in accordance with the present invention is a cell observation apparatus for observing a culturing process of cells according to an observation schedule designated by a user, the apparatus including: photographic means for photographing the cells according to the observation schedule; observation schedule acquisition means for acquiring a new observation schedule in response to an input of photographic conditions by the user; overlapping determination means for determining whether a photographing time of the photographic means included in the photographic conditions of the new observation schedule that has been acquired by the observation schedule acquisition means overlaps a photographing time of the photographic means included in the photographic conditions of an already registered observation schedule; change means for changing the photographic conditions of one or both of the observation schedules when the overlapping of the photographing times of the observation schedules has been determined by the overlapping determination means; and observation schedule registration means for registering the new observation schedule, or registering the new observation schedule and then re-registering the already registered observation schedule on the basis of the photographic conditions that are changed by the change means.

A cell observation method or a program in accordance with the present invention is a cell observation method for observing a culturing process of cells according to an observation schedule by which time lapse observation for a predetermined photographing time is performed at every predetermined photographing interval, or a program that causes a computer to execute processing of observing a culturing process of cells according to an observation schedule by which time lapse observation for a predetermined photographing time is performed at every predetermined photographing interval, including the steps of: presenting to a user an observation schedule that has already been registered; acquiring a photographing interval and a photographing time of a new observation schedule in response to an input of photographic conditions by the user; determining whether photographing times of the new observation schedule and the already registered observation schedule overlap on the basis of the photographing interval and the photographing time; and changing, in a case where the photographing times have been determined to overlap, the photographic conditions of the observation schedule by shifting the photographing time of one or both of the observation schedules back or forth within an allowed time range that has been set in advance, and registering the observation schedule.

In the cell observation apparatus in accordance with the present invention, the photographic means photographs the cells according to an observation schedule. Where a new observation schedule is acquired in response to the input of photographic conditions by the user, it is determined whether the photographing time of the photographic means included in the photographic conditions of the new observation schedule and the photographing time of the photographic means included in the photographic conditions of the already registered observation schedule overlap, and when the photographing times of the two observation schedules are determined to overlap, the photographic conditions including the photographing time in one or both of the observation schedules are changed. The new observation schedule is thereafter registered, or the new observation schedule is registered and the already registered observation schedule is re-registered on the basis of the changed photographic conditions.

In the cell observation method or program in accordance with the present invention, the observation schedule that has already been registered is presented to the user, and the photographing interval and photographing time of the new observation schedule are acquired in response to the input of photographic conditions by the user. Based on the photographing interval and photographing time, it is determined whether the photographing times in the new observation schedule and the already registered observation schedule overlap, and in a case where the photographing times are determined to overlap, the photographing time of one or both of the new observation schedules is shifted back or forth within an allowed time range that has been set in advance, thereby changing the photographic conditions of the observation schedule, and the observation schedule is registered.

According to one aspect for the present invention, the setting of schedules is facilitated.

BRIEF DESCRIPTION OF THE DRAWINGS

FIG. 7 shows an example of the set value input screen 160;

DESCRIPTION OF THE PREFERRED EMBODIMENTS

Embodiment 1

A specific embodiment using the present invention will be described below with reference to the appended drawings.

Figure 1:
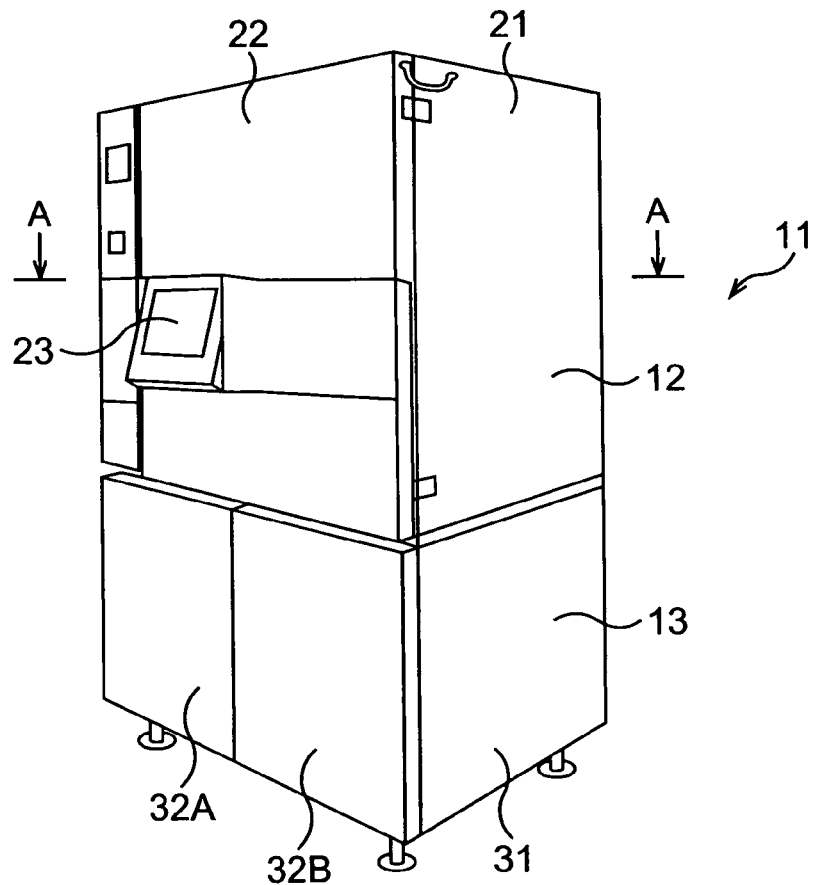
FIG. 1 is a perspective view illustrating a configuration of one embodiment of the cell observation apparatus that uses the present invention.

FIG. 1 is a perspective view illustrating a configuration of one embodiment of the cell observation apparatus in accordance with the present invention.

The cell observation apparatus can be used by a plurality of users (or one user can set a plurality of observation schedules), and each user can set an observation schedule (or a test schedule). In this case, overlap setting such that observation schedules overlap can be a problem. The following methods can be used to avoid overlap setting of observation schedules.

1. When observation schedules overlap, one or both users change photographic conditions to avoid overlapping.

2. An allowed time range is provided in photographic conditions of an observation schedule and the observation schedules are shifted in the allowed time range to avoid overlapping.

3. In a case where the apparatus is used by a plurality of users, a priority order of the users is set and the observation schedule of the user with a low priority order is changed to avoid overlapping.

4. The preset photographic location (number of points) that is a factor that determines the photographing time, a photographic magnification switching frequency, and a Z stocker number are changed to avoid the overlapping of observation schedules.

These overlapping avoidance methods will be described below in greater details.

Referring to FIG. 1, the cell observation apparatus 11 is constituted by an incubator unit 12 and a stand unit 13. The incubator unit 12 is disposed on top of the stand unit 13.

The incubator unit 12 is constituted by an incubator housing 21 and an incubator door 22. In the incubator unit 12, an inner space sealed by the incubator housing 21 and incubator door 22 is controlled so as to maintain an atmosphere suitable for cell culturing.

For example, the incubator housing 21 is provided with a temperature regulator using a Peltier element, a spraying device that sprays mist, a gas introducing unit that is connected to an external carbon dioxide cylinder, and an atmosphere sensor that detects atmosphere of the inner space (not shown in the figure). The incubator housing 21 and incubator door 22 have inside thereof a thermally insulating material. For example, the atmosphere of the inner space of the incubator housing 21 is maintained at a temperature of 37° C., a humidity of 90%, and a carbon dioxide concentration of 5%.

The incubator door 22 is attached to the incubator housing 21 so that the door can be opened and closed, and an operation panel 23 that is used to operate the cell observation apparatus 11 is provided at the surface of the incubator door.

The control panel 23 is, for example, a touch panel that is operated by the user. The display portion of the operation panel displays a GUI (Graphical User Interface) such as a schedule setting screen for setting an observation schedule for photographing the cells with a predetermined interval, a set value input screen for inputting set values of photographic conditions when a new observation schedule is added, and a photographing time setting screen for setting a photographing time on the basis of photographic magnification or photographic points. The operation panel 23 supplies the operation signals corresponding to the user's operations to the below-described control unit 44 shown in FIG. 3.

For example, at the set value input screen displayed on the operation panel 23, a photographing frequency in time lapse photography, a photographing time, and a photographing interval are inputted as photographic conditions of observation schedule. Further, the user names or attributes of the users that use the cell observation apparatus 11 can be registered in advance in the cell observation apparatus 11. When user registration is performed, the priority order of the users can be registered. For example, the priority order can be so set that the priority of the user who has been registered earlier is higher than that of the user who has been registered later.

Figure 3:
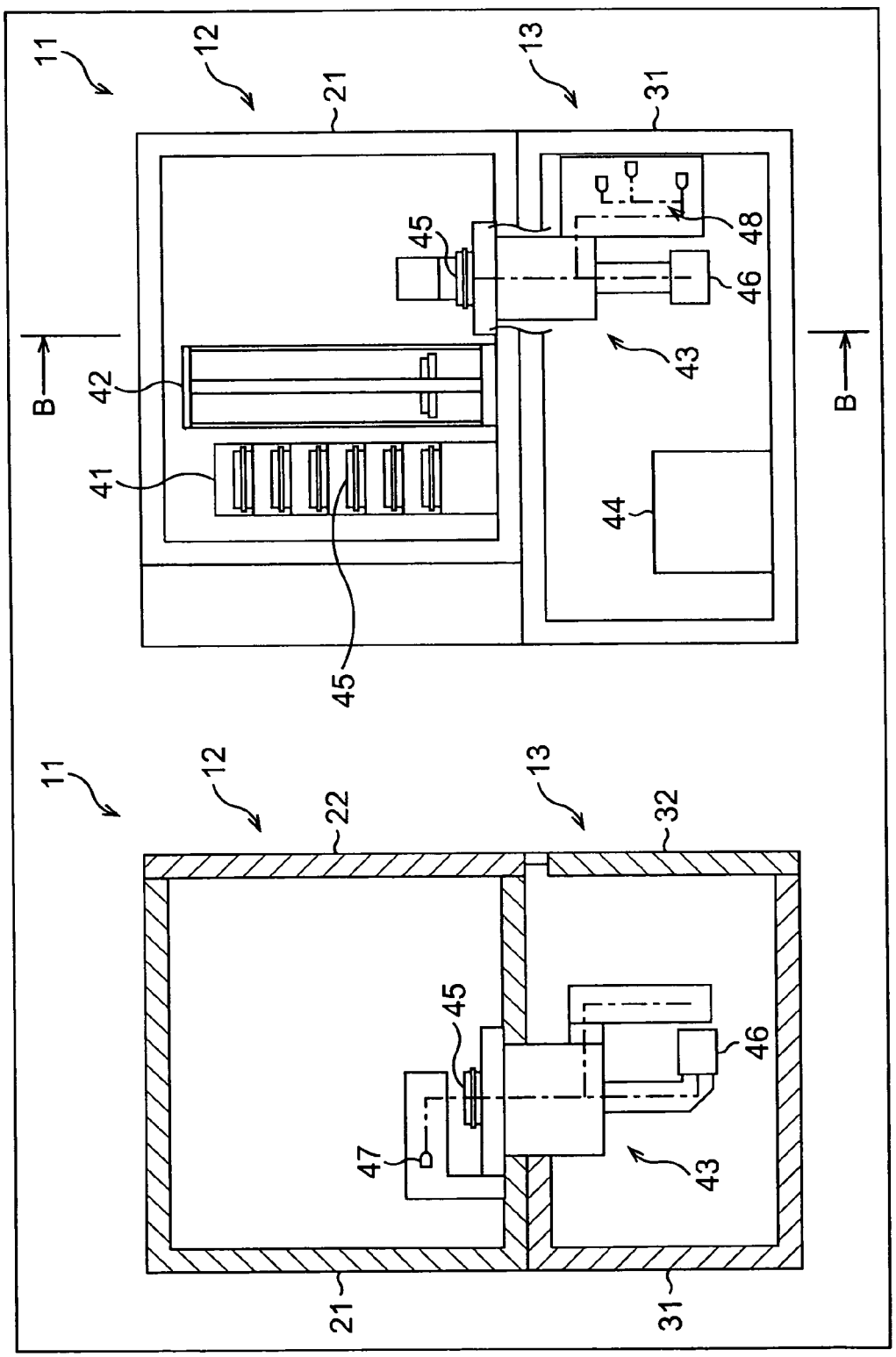
FIG. 3 is a front view and a cross-sectional view of the cell observation apparatus 11.

The stand unit 13 is constituted by a housing 31 and doors 32A and 32B. The doors 32A and 32B are attached to the housing 31 so that the doors can be opened and closed. The below-described LED 48 for fluorescence that are shown in FIG. 3 are accommodated inside the stand unit 13.

Figure 2:
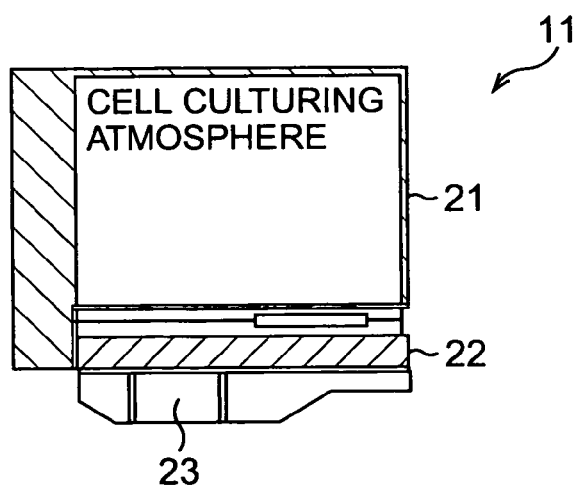
FIG. 2 is a cross-sectional view of the cell observation apparatus 11.

FIG. 2 is a cross-sectional view of the cell observation apparatus 11, as viewed from the direction of arrows A-A shown in FIG. 1.

As shown in FIG. 2, the inner space of the incubator unit 12 is sealed by the incubator housing 21 and incubator door 22. This inner space, that is, the space maintained under the atmosphere suitable for cell culturing, will be appropriately referred to hereinbelow as cell culturing atmosphere.

The configuration of the cell observation apparatus 11 shown in FIG. 1 will be explained below with reference to FIG. 3.

The right side in FIG. 3 is a front view of the cell observation apparatus 11 in a state in which the incubator door 22 and also doors 32A and 32B of the stand unit 13 are taken off. The left side in FIG. 3 is a cross-sectional view of the cell observation apparatus 11, as viewed from the direction of arrows B-B in the front view.

Referring to FIG. 3, the cell observation apparatus 11 is constituted by a stocker unit 41, a conveying unit 42, an observation unit 43, and the control unit 44.

The stocker unit 41 and conveying unit 42 are accommodated in the cell culturing atmosphere of the incubator unit 12. The upper portion of the observation unit 43 is accommodated in the cell culturing atmosphere of the culturing unit 12, and the lower portion of the observation unit 43 is accommodated inside the stand unit 13. The control unit 44 is accommodated inside the stand unit 13.

A plurality of culturing containers 45 containing cells that are to be incubated are accommodated in the stocker unit 41. In the stocker unit 41, as shown in FIG. 3, a plurality of shelves that carry the culturing containers 45 are provided in the vertical direction. A plurality of the culturing containers 45 can be loaded in the depth direction onto each shelf.

The conveying unit 42 conveys the predetermined culturing container 45 from the stocker unit 41 to the observation unit 43 under the control of the control unit 44.

The observation unit 43 is provided with a photographic unit 46 that photographs the cells cultured in the culturing unit 45, a LED 47 for transmitted light that irradiates the cells cultured in the culturing containers 45 with light, and the LED 48 for fluorescence and serves to photograph the cells cultured in the culturing containers 45. As shown in FIG. 3, the LED 47 for transmitted light are disposed in the cell culturing atmosphere of the incubator unit 12, whereas the photographic unit 46 and LED 48 for fluorescence are disposed inside the stand unit 13 that is located outside the cell culturing atmosphere of the incubator unit 12.

The LED 47 for transmitted light emit light, for example, in a wavelength range of 600 to 660 nm, the light from the LED 47 for transmitted light is transmitted through the cells of the culturing containers 45, and a phase difference image created by the transmitted light is picked up with the photographic unit 46. The LED 48 for fluorescence emit light (excitation light) with a wavelength that excites a fluorescent substance correspondingly to the fluorescent substance contained in the cells cultured in the culturing container 45, and a fluorescence image created by the fluorescence of the fluorescent substance induced by the light from the LED 48 for fluorescence is picked up by the photographic unit 46.

An operation signal corresponding to the user's operation is supplied from the operation panel 23 shown in FIG. 1 to the control unit 44, and the control unit 44 controls the units of the cell observation apparatus 11 in response to the user's operation.

For example, the control unit 44 control the conveying unit 42, and the predetermined culturing container 45 accommodated in the stocker unit 41 is conveyed to the observation unit 43. Further, the control unit 44 controls the operation panel 23, and a GUI such as the schedule setting screen and photographing time setting screen is appropriately displayed at the display unit of the operation panel 23. The control unit 44 also controls the temperature regulator, spraying device, and gas introducing unit provided in the incubator housing 21, so that the cell culturing atmosphere is maintained at constant temperature, humidity, and carbon dioxide concentration in response to the outputs of the atmosphere sensors provided in the incubator housing 21.

Figure 4:
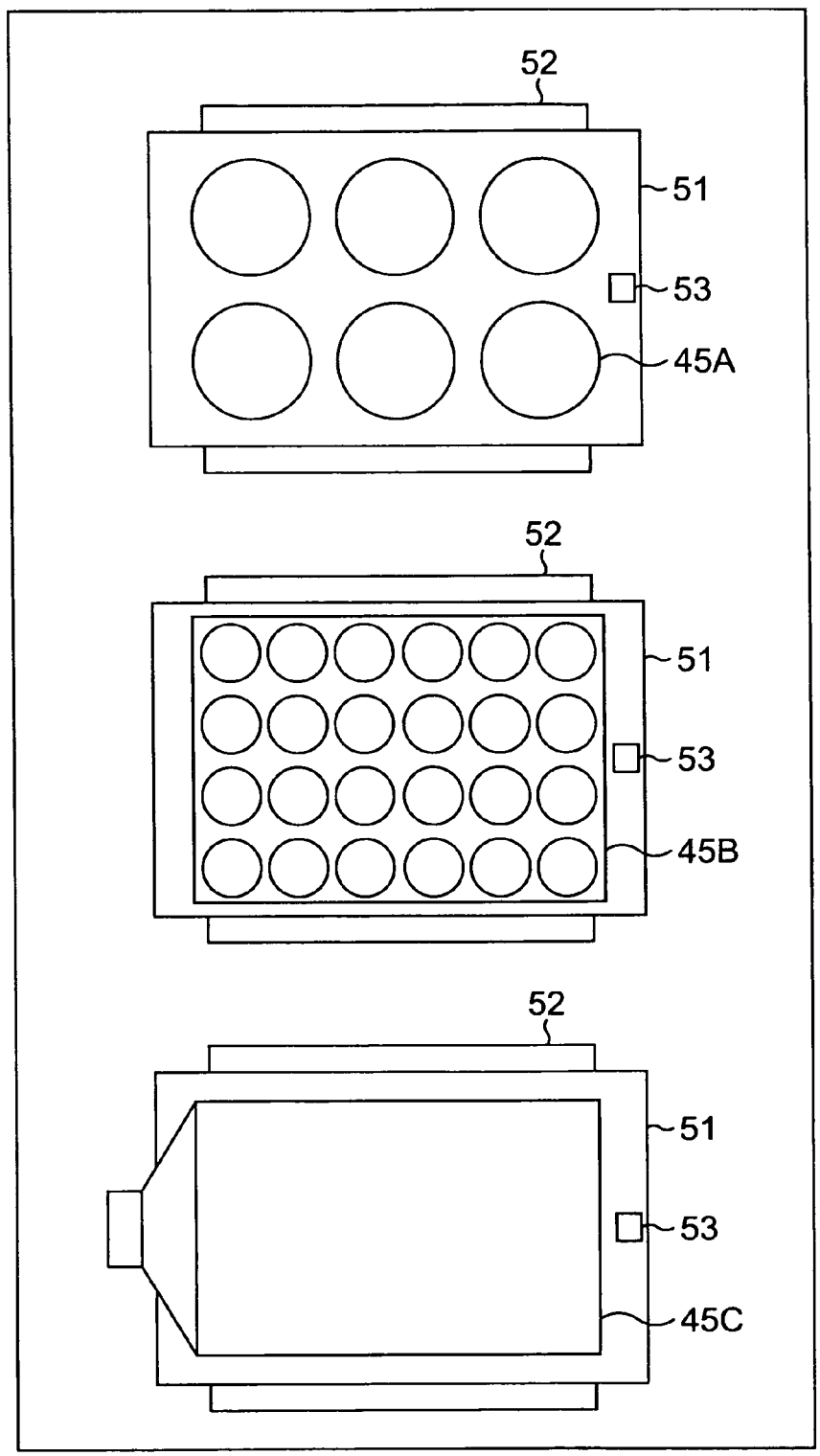
FIG. 4 shows an example of the culturing container 45.

FIG. 4 is an example of the culturing container 45 into which cells that are to be cultured are introduced.

For example, a dish 45A, a well plate 45B, or a flask 45C is used as the culturing container 45. First from the top in FIG. 4 are six dishes 45A, second from the top in FIG. 4 is the well plate 45B having 24 wells, and third from the top (the lowest) in FIG. 4 is the flask 45C.

The dish 45A, well plate 45B, or flask 45C is held with a holder 51, and a support piece 52 that is used during conveying with the conveying unit 42 is provided in the holder 51.

Further, the holder 51 is provided with an identification marker 53 for identifying the respective culturing container 45 (dish 45A, well plate 45B, or flask 45C). For example, the user (researcher) of the culturing container 45 is specified by the identification marker 53, and the culturing containers 45 are managed for each user. Therefore, the culturing container 45 of another user is controlled (managed) so that it cannot be freely taken out.

Figure 5:
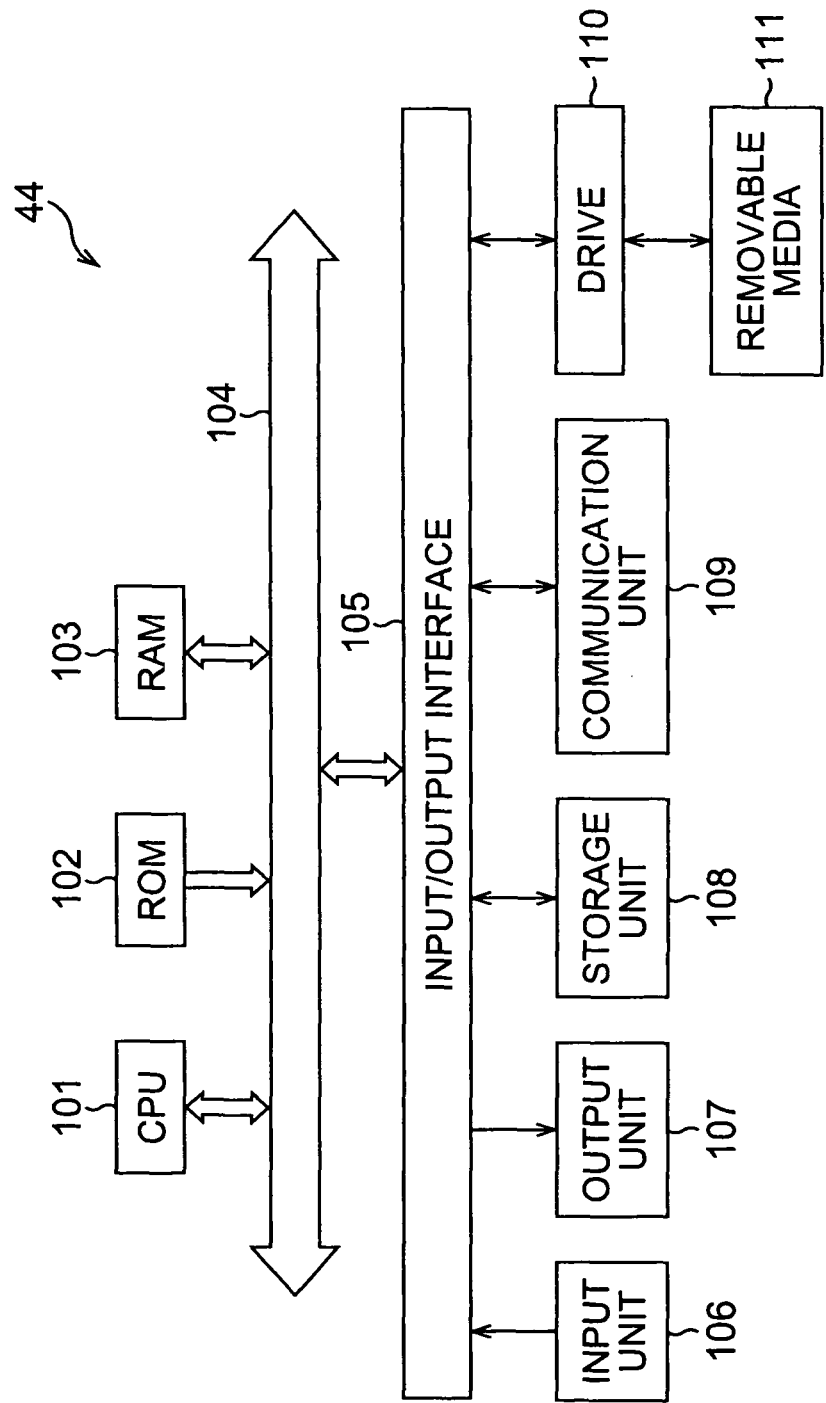
FIG. 5 is a block diagram illustrating a configuration example of the control unit 44.

FIG. 5 is a flow diagram illustrating a configuration example of the control unit 44 shown in FIG. 3.

In FIG. 5, the control unit 44 is constituted by a CPU (Central Processing Unit) 101, a ROM (Read Only Memory) 102, a RAM (Random Access Memory) 103, a bus 104, an input/output interface 105, an input unit 106, an output unit 107, a storage unit 108, a communication unit 109, and a drive 110.

The CPU 101, ROM 102, and RAM 103 are connected to each other by a bus 104, and the input/output interface 105 is also connected to the bus 104. In addition to the bus 104, the input unit 106, output unit 107, storage unit 108, communication unit 109, and drive 110 are also connected to the input/output interface 105.

The CPU 101 executes the processing of various types according to a program stored in the ROM 102 or a program loaded from the storage unit 108 into the RAM 103 via the input/output interface 105 and bus 104. The ROM 102 stores the program that is to be executed by the CPU 101. The RAM 103 appropriately stores the program that is to be executed by the CPU 101 or data necessary for the CPU 101 to execute the processing of various types.

The input unit 106 is connected to an input device or operation button of a touch panel present at the operation panel 23 shown in FIG. 1, acquires operation signals corresponding to the user's operation of the input device or operation button of the touch panel, and supplies the operation signal to the CPU 101 via the input/output interface 105 and bus 104.

The output unit 107 is connected to the display device of the touch panel present at the operation panel 23 shown in FIG. 1 and displays a GUI such as the schedule setting screen and photographing time setting screen on the display unit of the touch panel according to the control of CPU 101.

The storage unit 108 is constituted by a hard disk or a flash memory and stores data such as a program to be executed by the CPU 101 or a registered schedule.

The communication unit 109 is constituted by a modem, a terminal adapter, or other communication interface and performs communication processing via networks of various types (not shown in the figure) including Internet, LAN (Local Area Network), telephone like, or CATV (cable television). For example, when a computer (not shown in the figure) is connected to the control unit 44 via the communication unit 109, the user can set a schedule or photographic conditions via the computer.

A removable media 111 composed of a magnetic disk, an optical disk, a magnetooptical disk, or a semiconductor memory is appropriately installed in the drive 110. The drive 110 reads data recorded on the removable media 111 or records predetermined data onto the removable media 111. Where the removable media 111 having recorded thereon a program that is to be executed by the CPU 101 is installed in the drive 110, this program is read by the drive 110 and installed, as necessary, in the storage unit 108 via the input/output interface 105. The program to be executed by the CPU 101 can be installed in the storage unit 108 via the above-described removable media 111 and also can be installed in the storage unit 108 by downloading from a download site via the communication unit 109.

Figure 6:
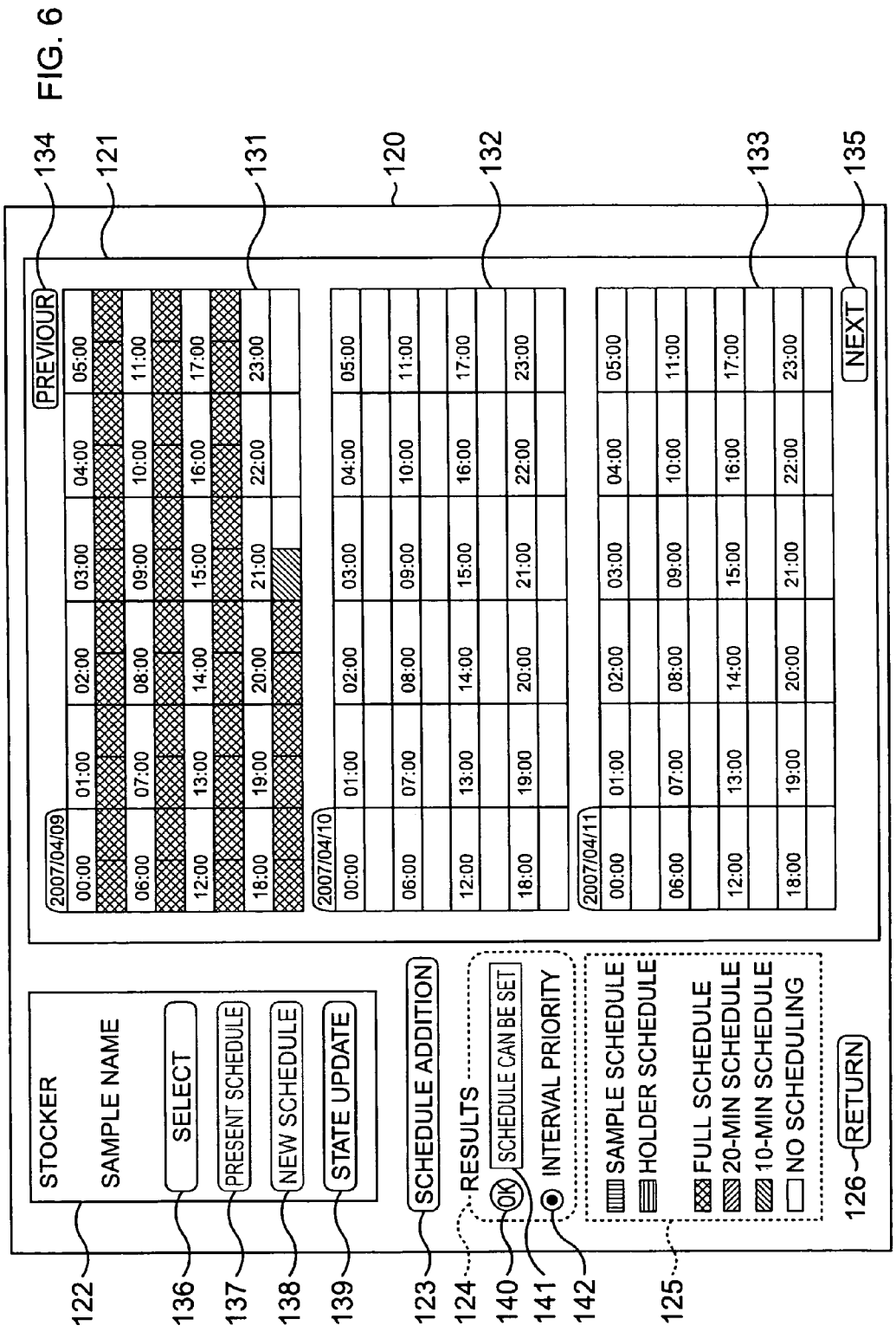
FIG. 6 shows an example of the schedule setting screen 120.

FIG. 6 shows an example of a schedule setting screen that is displayed on the operation panel 23 shown in FIG. 1.

Referring to FIG. 6, a time schedule display section 121, a sample information display section 122, a schedule addition button 123, a result display section 124, a schedule display example display section 125, and a return button 126 are displayed at the schedule setting screen 120.

In the time schedule display section 121, the time schedule from 0 hr to 24 hr is displayed for each day, and hatching according to the display example that is displayed in the schedule display example display section 125 is performed for a time interval for which the schedule has already been registered.

More specifically, a time schedule 131 for Apr. 9, 2007, a time schedule 132 for Apr. 10, 2007, and a time schedule 133 for Apr. 11, 2007 are displayed at the time schedule display section 121. The time schedules 131 to 133 divided in 1 hr intervals, and the registered schedule is displayed by hatching in 30-min units.

In the time schedule 131, the hatching that indicates that the schedule is registered as a full schedule from a time of "00:00" to a time of "20:00" and the hatching that indicates that the schedule is registered as a 10-min schedule from a time of "21:00" to a time of "21:30" are performed. The time schedule 131 thus indicates that the schedules corresponding to respective hatched zones have already been registered.

Further, a previous button 134 that causes the display of the time schedule of the previous day is displayed in the upper right corner of the time schedule display section 121, and a next button 135 that causes the display of the time schedule of the next day is displayed in the lower right corner of the time schedule display section 121.

The sample information display section 122 has displayed therein a select button 136 that is operated when the user selects the culturing container 45 that is the object of observation, a present schedule button 137 that is used to display the schedule that is presently registered for the culturing container 45, a new schedule button 138 that is used to display a set value input screen 160 (below-described FIG. 7) that serves to input the set values of photographing conditions of the new schedule for the culturing container 45, and a state update button 139 that is used to update the display of the state of the schedule for the culturing container 45.

The schedule addition button 123 is operated when the user completes the input of set values of photographic conditions of a new schedule to the set value input screen 160. Where the schedule addition button 123 is operated, the CPU 101 (FIG. 4) performs the detection of overlapping of the photographing time of the new schedule and the photographing time of the registered schedule on the basis of set values that have been inputted to the set value input screen 160.

The result display section 124 has displayed therein a detection result display button 140 that displays whether a new schedule can be added based on the results obtained in detecting the overlapping of the photographing time of the new schedule and the photographing time of the registered schedule, a message window 141 that presents a change of the schedule when the new schedule cannot be added, and a radio button 142 that allows the user to indicate whether to fix preferentially the photographing interval time (interval) when the addition of new schedule is impossible and the change of schedule is presented.

For example, when the radio button 142 is selected in a case where the photographing time overlapping has been detected, the photographing interval is preferentially fixed and, therefore, the processing of changing (reducing) the photographing time to avoid the overlapping of photographing time is performed. By contrast, where the radio button 142 has not been selected, the processing of shifting (moving) the photographing time to avoid the overlapping of photographing time is performed (thus, in this case, the photographing interval is changed).

A display example of hatching that represents a state of the registered schedule that is displayed in the time schedules 131 to 133 is displayed in the schedule display example display section 125. Examples of schedule state include sample schedule, holder schedule, full schedule, 20-min schedule, 10-min schedule, and no scheduling, and a different hatching is used for each state. In the example shown in FIG. 6, no hatching is performed in the no scheduling state. The schedule state may be represented not only by hatching, but also by different colors.

The return button 126 is operated when a screen that has been displayed before the display of the schedule setting screen 120 is displayed at the operation panel 23.

FIG. 7 shows an example of a set value input screen for inputting a set value of a new schedule.

In FIG. 7, list buttons 161 and 162 and combo boxes 163 to 166 are displayed at the set value input screen 160.

In the list box 161, hours of photographing interval that indicate an interval for photographing in the time lapse photography are listed up, and the user selects the hours of photographing interval from this list. In the list box 162, minutes of photographing interval are listed up, and the user selects the minutes of photographing interval from this list. The photographing interval (hours and minutes) that is set by the list boxes 161 and 162 is appropriately called "photographing interval".

In the combo box 163, a photographing time list is displayed when the user operates the arrow button at the right end of the combo box. The user selects the photographing time from this list.

The combo box 164 is composed of a plurality of combo boxes that list up a photographing start year, a photographing start month, a photographing start day, a photographing start hour, and a photographing start minute. By using the respective combo box, the user selects the photographing start year, photographing start month, photographing start day, photographing start hour, and photographing start minute. The combo box 165 is composed of a plurality of combo boxes that list up a photographing end year, a photographing end month, a photographing end day, a photographing end hour, and a photographing end minute. By using the respective combo box, the user selects the photographing end year, photographing end month, photographing end day, photographing end hour, and photographing end minute.

The combo box 166 is a box that sets an allowed time range in which a shift (movement) of the photographing time is allowed when the overlapping of a photographing time of the new schedule and the photographing time of the already registered schedule is detected. Thus, when the overlapping of a photographing time of the new schedule and the photographing time of the already registered schedule is detected, the photographing time of one or both of the schedules is shifted within the allowed time range that has been set for these schedules, thereby avoiding the overlapping of the photographing time.

As for the allowed time, for example, a predetermined ratio to a set value of the photographing time that is a photographing condition in the time lapse photography, more specifically, a time of a 10% to 20% ratio is determined by automatic calculations and displayed in the combo box 166. Alternatively, the user is allowed to conduct manual input within a range of a time of a 10% to 20% ratio with respect to the set value of the photographing interval with the combo box 166, and the user inputs the allowed time by operating the combo box 166.

Further, where the user inputs the photographing interval, photographing time, photographing period (photographing start time and photographing end time), and allowed time with the set value input screen 160 and operates the schedule addition button 123 shown in FIG. 6, the detection of photographing time overlapping is performed. For example, when the overlapping of photographing time is not detected, the possibility of setting a new schedule is displayed on the result display section 124 of the schedule setting screen 120.

Figure 8:
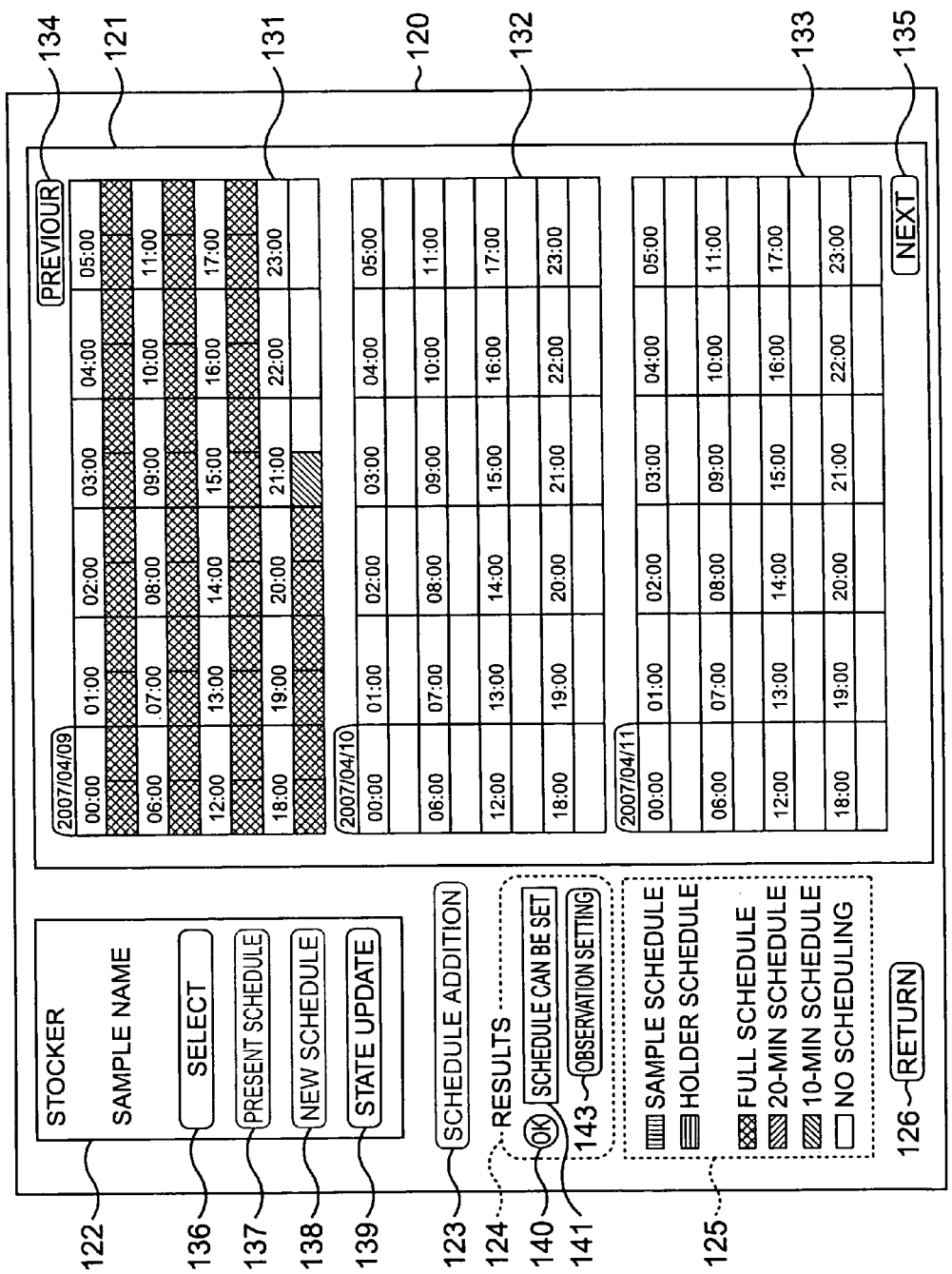
FIG. 8 shows an example of the schedule setting screen 120.

Thus, FIG. 8 shows an example of the schedule setting screen 120 when the new schedule can be set.

As shown in FIG. 8, "OK" that indicates that the new schedule can be set is displayed at the detection result display button 140 of the result display section 124, and "schedule can be set" is displayed in the message window 141. Further, in the result display section 124, an observation setting button 143 is displayed instead of the radio button 142 (FIG. 8). Where the user operates the observation setting button 143, the new schedule is set, that is, stored (registered) in the storage unit 108 shown in FIG. 4.

In a case where the detection of photographing time overlapping is performed, for example, when the photographing time overlapping is detected, the impossibility of setting a new schedule is displayed on the result display section 124 of the schedule setting screen 120.

Figure 9:
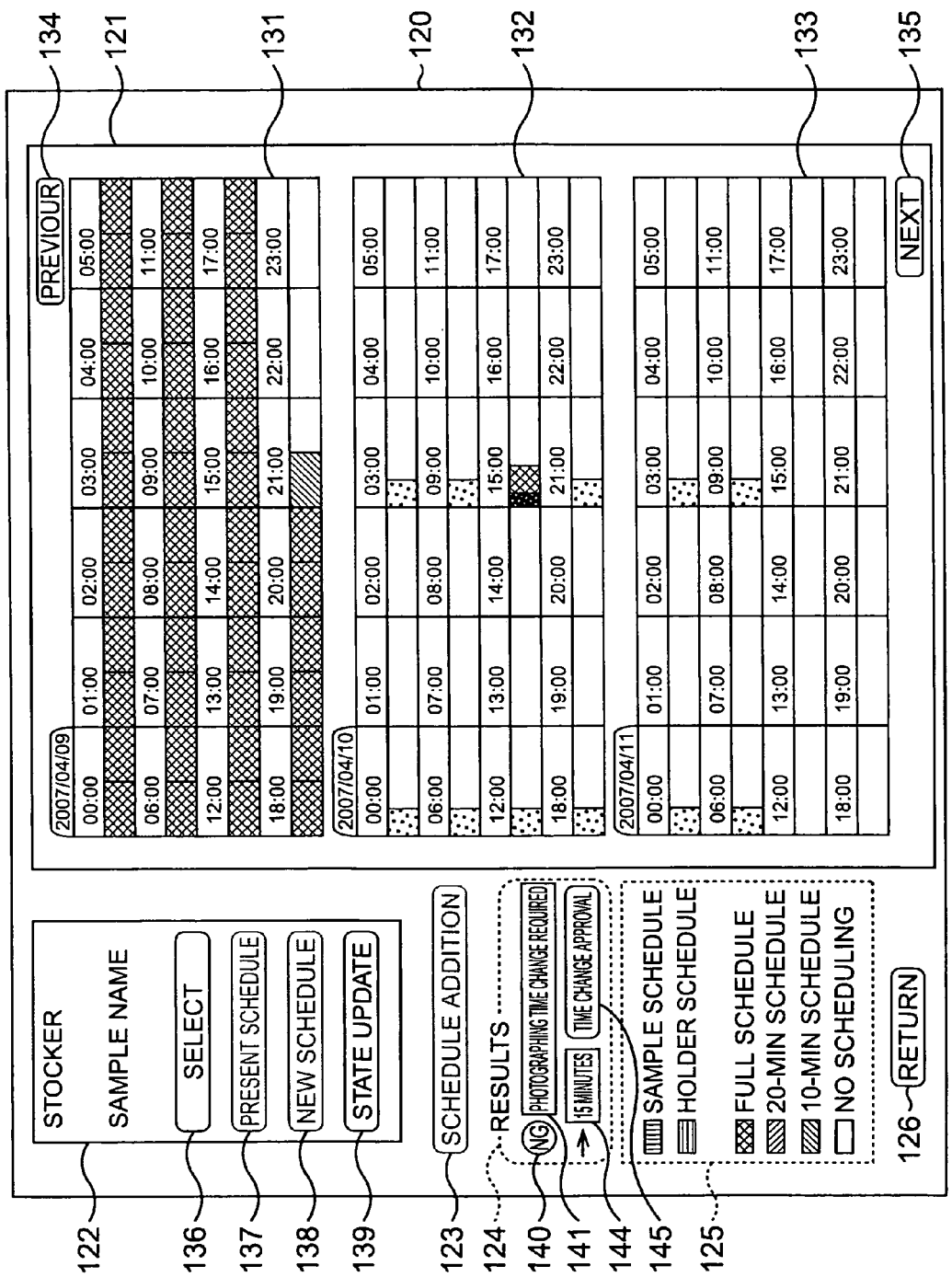
FIG. 9 shows an example of the schedule setting screen 120.

Thus, FIG. 9 shows an example of the schedule setting screen 120 when the new schedule cannot be set.

As shown in FIG. 9, "NG" that indicates that the new schedule cannot be set is displayed at the detection result display button 140 of the result display section 124, and "photographing time change is required" is displayed in the message window 141. Further, in the result display section 124, a message window 144 and a time change approval button 145 are displayed instead of the radio button 142 (FIG. 8).

Here, for example, in a case where a schedule has already been registered from a time of "15:15" to a time of "15:30" on Apr. 10, 2007, as shown in the time schedule 132 in FIG. 9 and the user inputs set values such as to perform a time lapse photography with a photographing time of 20 min and a photographing interval of 3 h in a photographing period of from a time of "00:00" on Apr. 10, 2007, to a time of "09:00" on Apr. 11, 2007, a 5-min overlapping of photographing time from a time of "15:15" to a time of "15:20" on Apr. 10, 2007, is detected. In this case, for example, photographing can be performed within 15 min from a time of "15:00" to a time of "15:15" on Apr. 10, 2007. Therefore, "15 min" is displayed in the message window 144, and hatching is performed that displays a photographing time after the change of 15 min from a time of "15:00" to a time of "15:15" on Apr. 10, 2007.

In a case where the user approves of such a change of the photographing time, the user sets a new schedule with a changed photographing time by operating the time change approval button 145.

In this case, at the schedule setting screen 120 shown in FIG. 9, the radio button 142 of the schedule setting screen 120 shown in FIG. 6 is selected, and when a schedule change is presented, the button is displayed in a case where the photographing interval is preferentially fixed.

In a case where the radio button 142 of the schedule setting screen 120 shown in FIG. 6 is not selected, the setting is not made so as to fix preferentially the photographing interval. In other words, the settings are made such that the photographing time is preferably fixed and the photographing interval may be changed by shifting the photographing time. In this case, when a schedule change is presented, a processing is performed to shift the photographing time for which overlapping has been detected within the allowed time range.

Thus, as has been explained with reference to FIG. 7, when the schedule set values are inputted, an allowed time is set with the combo box 166, and the processing of shifting the photographing time for which the overlapping has been detected is performed within the allowed time range. Where the overlapping of the photographing time is avoided by such a processing, the new schedule can be registered.

Figure 10:
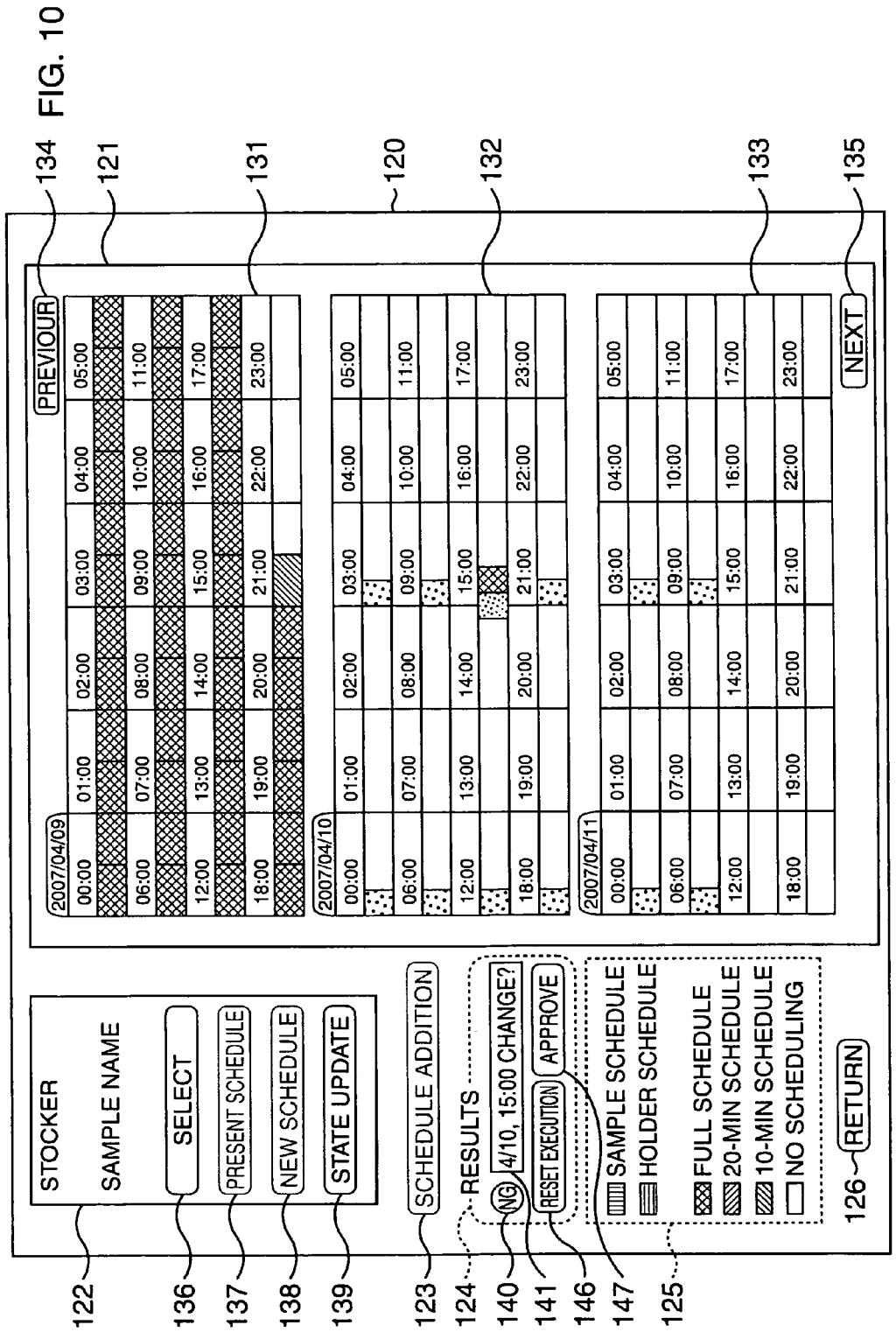
FIG. 10 shows an example of the schedule setting screen 120.

FIG. 10 shows an example of a schedule setting screen 120 in which a photographing time that can be registered is presented to the user as a result of processing performed to shift the photographing time.

As shown in FIG. 10, "NG" is displayed at the detection result display button 140 of the result display section 124, and "4/10, 15:00 CHANGE?" is displayed in the message window 141. Further, a reset execution button 146 and an approval button 147 are displayed in the result display section 124.

For example, as shown by the time schedule 132 in FIG. 10, in a case where a schedule has already been registered from a time of "15:15" to a time of "15:30" on Apr. 10, 2007, when the user inputs set values so as to perform time lapse photography in a photographing period from a time of "00:00" on Apr. 10, 2007, to a time of "09:00" on Apr. 11, 2007, with a photographing interval of 3 h, and a photographing time of 20 min, the 5-min overlapping of photographing times from a time of "15:15" to a time of "15:20" on Apr. 10, 2007, is detected.

In this case, where the allowed time of the new schedules is assumed to be set to 15 min, a processing of shifting the photographing time for which the overlapping has been detected is performed, the photographing time is shifted to 20 min from a time of "14:55" to a time of "15:15" on Apr. 10, 2007, and the respective time zone is hatched. Thus, a processing is performed by which the photographing time is shifted by the shortest time necessary to avoid the overlapping within the time range that has been set as an allowed time range. In this example, a processing of shifting by 5 min is performed.

In a case where the user approves of the photographing time that has thus been shifted, the user operates the approval button 147, and where the setting of the photographing time is performed again, operates the reset execution button 146.

In a case where the approval button 147 is operated, a new schedule for which the photographing time has been changed is set (registered), and where the reset execution button 146 is operated, the set value input screen 160 shown in FIG. 7 is displayed again.

In some cases the overlapping of photographing times is not avoided even when the processing is executed by which the photographing time for which the overlapping has been detected is shifted within the allowed time that has been set for the new schedule. In such cases, the schedule setting screen 120 is displayed that presents the overlapping state after the photographing time has been shifted within the allowed time range (that is, shifted by a maximum limit time for which shifting is allowed).

Figure 11:
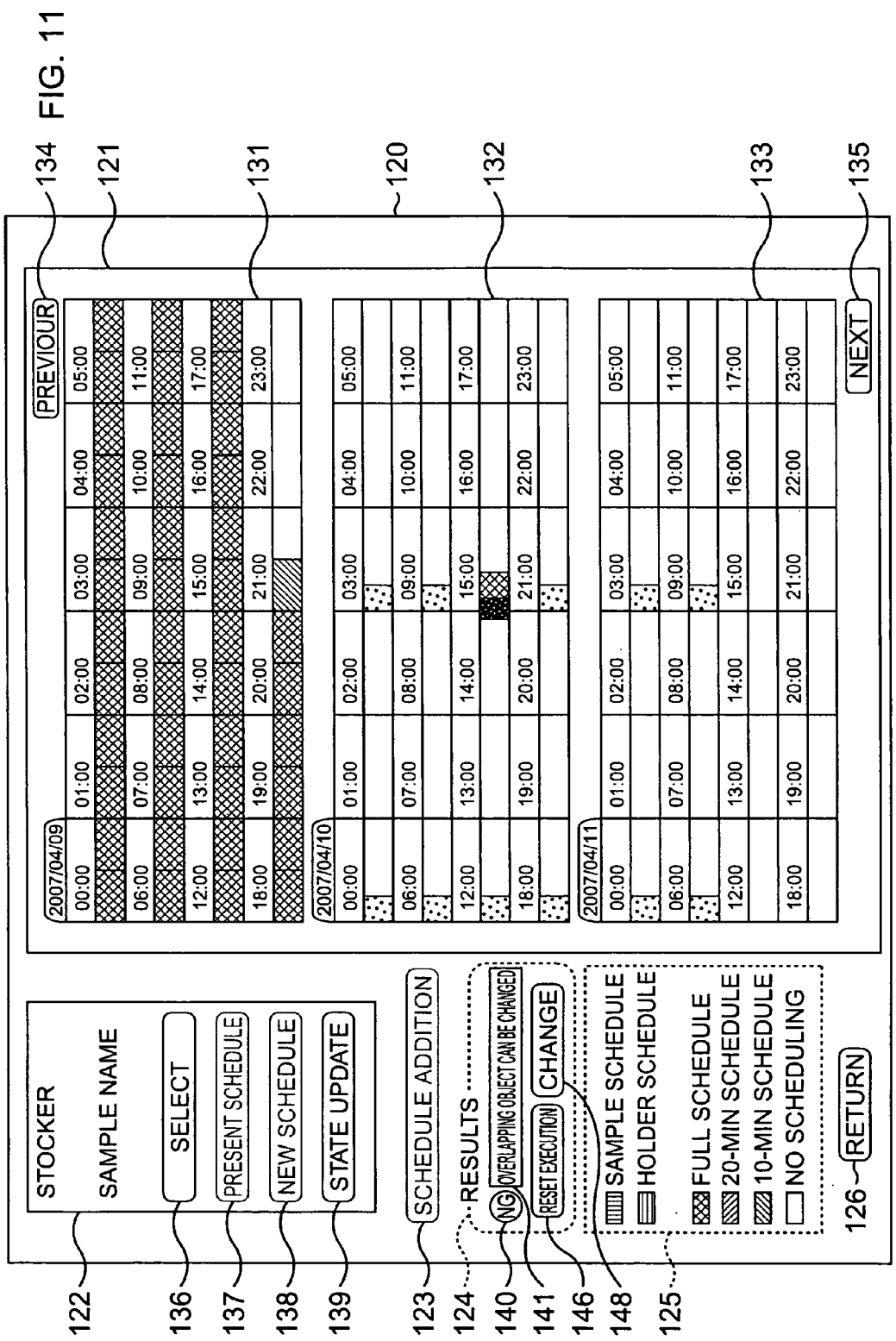
FIG. 11 shows an example of the schedule setting screen 120.

FIG. 11 shows an example of the schedule setting display 120 that presents the overlapping state when the overlapping cannot be avoided even by performing the processing of shifting the photographing time.

As shown in FIG. 11, "NG" is displayed at the detection result display button 140 of the result display section 124, and "overlapping object can be changed" is displayed in the message window 141. Further, the reset execution button 146 and change button 148 are displayed in the result display section 124.

The message "overlapping object can be changed" is displayed in the message window 141, as in the schedule setting display 120 shown in FIG. 11, when the priority order of the user that has registered the photographing time (appropriately referred to hereinbelow as "overlapping object") of the already registered schedule that overlaps the photographing time of the new schedule is not higher than the priority order of the user of the new schedule (that is, equal to or lower than the priority order of the user of the new schedule) and the schedule that is an overlapping object is not set to fix preferentially the photographing interval.

Where the user operates the change button 148, information of the overlapping object (the user that has registered the schedule that is the overlapping object, or the allowed time set for this schedule) is displayed, and if the user allows the overlapping object to be shifted, a processing of shifting the overlapping object is performed. For example, the photographing time of the already registered schedule that is from a time of "15:15" to a time of "15:30" on Apr. 10, 2007, is shifted back within the allowed time range that has been set for this schedule.

In a case where the overlapping object is not shifted, the user displays again the set value input screen 160 shown in FIG. 7 by operating the reset execution button 146, confirms the overlapping state shown in the schedule setting screen 120 shown in FIG. 11, and re-inputs the set values so as to avoid the overlapping of schedules.

Where the photographic conditions of the new schedule that does not overlap the already registered schedule are thus determined by using the schedule setting screen 120 and set value input screen 160, the photographing time setting screen 170 for setting the photographic conditions such as photographic magnification and photographic points is displayed at the operation panel 23.

Figure 12:
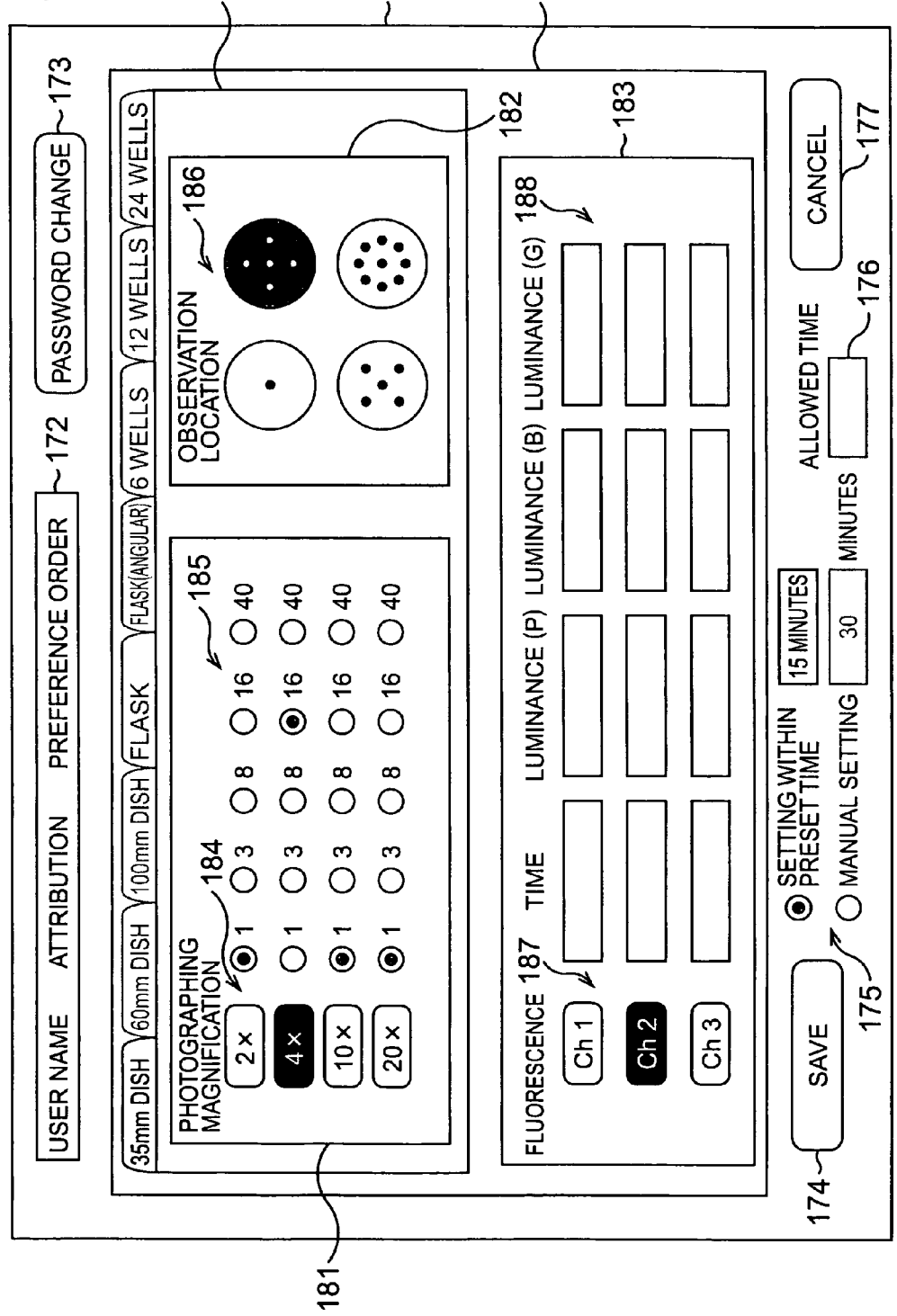
FIG. 12 shows an example of the photographing time setting screen 170.

FIG. 12 shows an example of the photographing time setting screen 170 for setting the photographing time.

As shown in FIG. 12, a photographic conditions setting section 171, a user information display section 172, a password change button 173, a save button 174, a radio button 175, an allowed time display section 176, and a cancel button 177 are displayed at the photographing time setting screen 170.

A culturing container designation frame 180, a photographic magnification and Z stack number display section 181, an observation location display section 182 that shows a photographic location (photographic point), and an illumination condition display section 183 are displayed at the photographic condition setting section 171.

The culturing container designation frame 180 is provided with a plurality of tabs for displaying the types of culturing containers 45, and the type of the culturing container 45 is designated by selecting the respective tab. As shown in FIG. 4, the dish 45A, well plate 45B, and flask 45C represent the types of the culturing containers 45. The tabs of the culturing container designation frame 180 makes it possible to designate any of a 35-mm dish, a 60-mm dish, a 100-mm dish, a round flask, an angular flask, a 6-well well plate, a 12-well well plate, and a 24-well well plate.

A plurality of photographic magnification buttons 184 for selecting a photographic magnification and a plurality of radio buttons 185 for selecting a Z stack number are displayed in the photographic magnification and Z stack number display section 181.

The photographic magnification is changed by switching the objective lens of respective magnification, and a photographic magnification of ×2, ×4, ×10, or ×20 can be selected with the photographic magnification buttons 184.

The Z stack number is the number of photographic sites in the Z direction (vertical direction; direction along the optical axis of cell observations) of cells inside the culturing container 45, and 1, 3, 8, 16, or 40 Z stacks can be selected with the radio button 185 for each ×2, ×4, ×10, or ×20 photographic magnification button 184.

Four observation location selection buttons 186 are displayed at the observation selection display section 182. One, five, and nine locations can be selected as the observation locations, and photographs are taken in locations disposed in the X and Y directions (directions perpendicular to the optical axis of cell observations) as shown in the four observation location selection buttons 186.

A channel selection button 187 and a text box 188 are displayed at the illumination condition display section 183.

A combination of illumination time and illumination brightness that have been inputted into the text box 188 is selected with the channel selection button 187, and the LED 48 for fluorescence are excited and emit light at the illumination time and illumination brightness selected with the channel selection button 187.

The illumination time and illumination brightness are inputted in the text box 188. The cell observation apparatus 11 is provided, for example, with three LED 48 for luminescence, and the three LED 48 for luminescence emit, for example, excitation light of 440 to 460 nm, excitation light of 460 to 490 nm, and excitation light of 520 to 550 nm. In the illumination brightness in the text box 188, a set value is inputted for each of the three LED 48 for luminescence that emit excitation light of 440 to 460 nm, excitation light of 460 to 490 nm, and excitation light of 520 to 550 nm.

Further, for example, the photographic magnification and Z stack number display section 181, observation location display section 182, and illumination condition display section 183 can be set in the order of description. For example, in the initial state, the photographic magnification and Z stack number display section 181 is active, and the observation location display section 182 and illumination condition display section 183 are inactive. Where the photographic magnification and Z stack number are selected with the photographic magnification and Z stack number display section 181, the observation location display section 182 becomes active, the observation location is selected in the observation location display section 182, and if the photographing time required for photographing in these locations is within the photographing time that has been set at the set value input screen 160 shown in FIG. 7, the illumination condition display section 183 becomes active.

The user name and attribution and also the priority order of the users that have been registered heretofore are displayed as information of the user of the culturing container 45 that has been selected as the observation object at the user information display section 172. The password change button 173 is operated by the user when the user changes a password necessary to use the cell observation apparatus 11. The save button 174 is operated to save the set values that have been selected or inputted in the photographic condition display unit 171.

Figure 13:
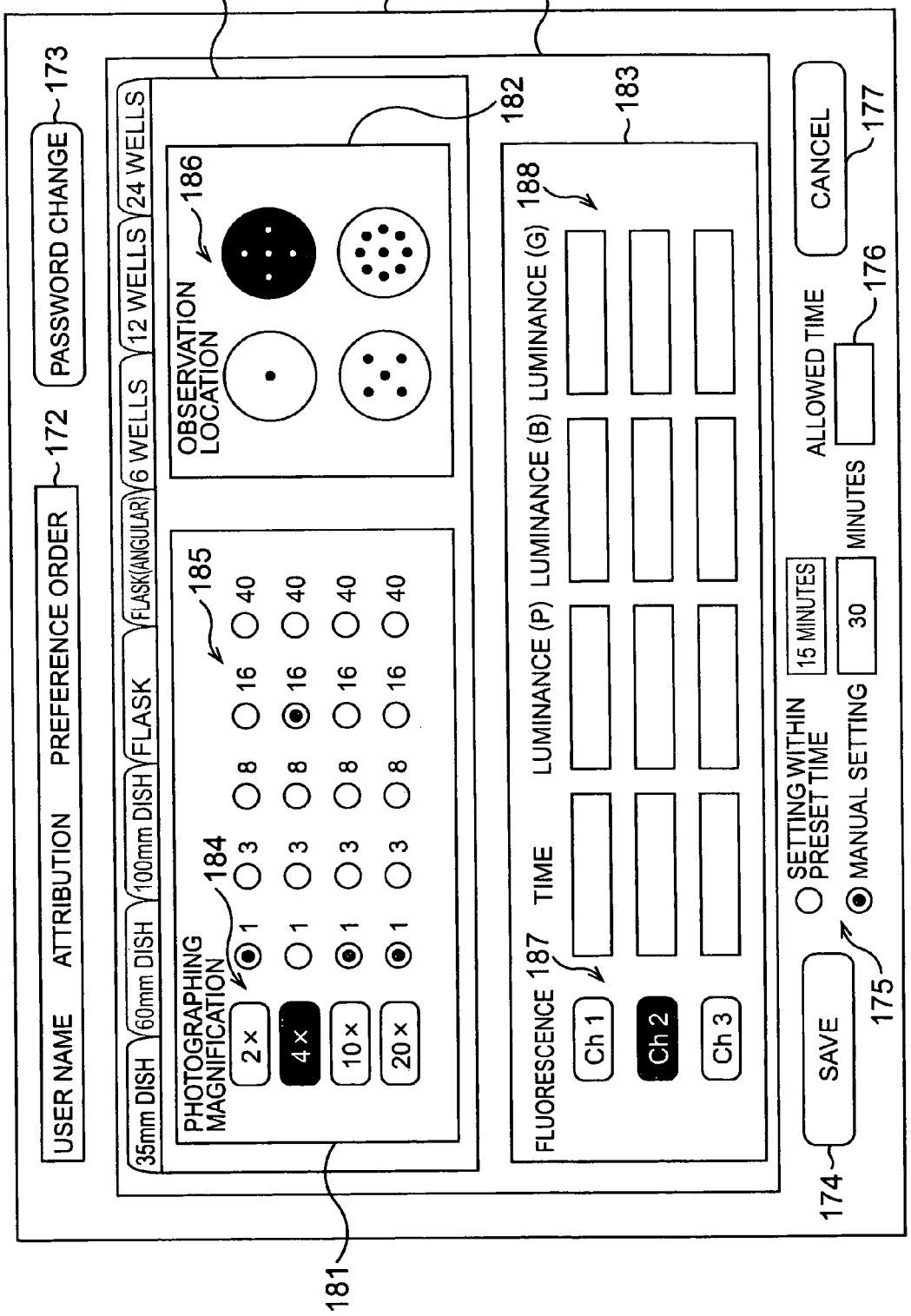
FIG. 13 shows an example of the photographing time setting screen 170.

Based on selection with the radio button 175, the time required for photographing according to the photographic conditions that are set in the photographic condition display section 171 is fitted either in a specified time range (photographing time that has been set with the set value input screen 160 shown in FIG. 7) or in a time range that is randomly set by the user. In the example shown in FIG. 12, an interval of 15 min is set as the specified time and the selection is made to fit the time required for photographing according to the photographic conditions that are set in the photographic condition display section 171 in the specified time range. In a case where the observations are performed within a time range that is randomly set by the user, without relying on a specified time, the photographing time can be set in the photographing time setting screen 170, and FIG. 13 shows the photographing time setting screen 170 that displays a time of "30 min" inputted manually by the user.

An allowed time that has been set with the combo box 166 shown in FIG. 7 is displayed in the allowed time display section 176. The cancel button 177 is operated when the settings of photographic conditions are canceled with the photographing time setting screen 170.

Figure 14:
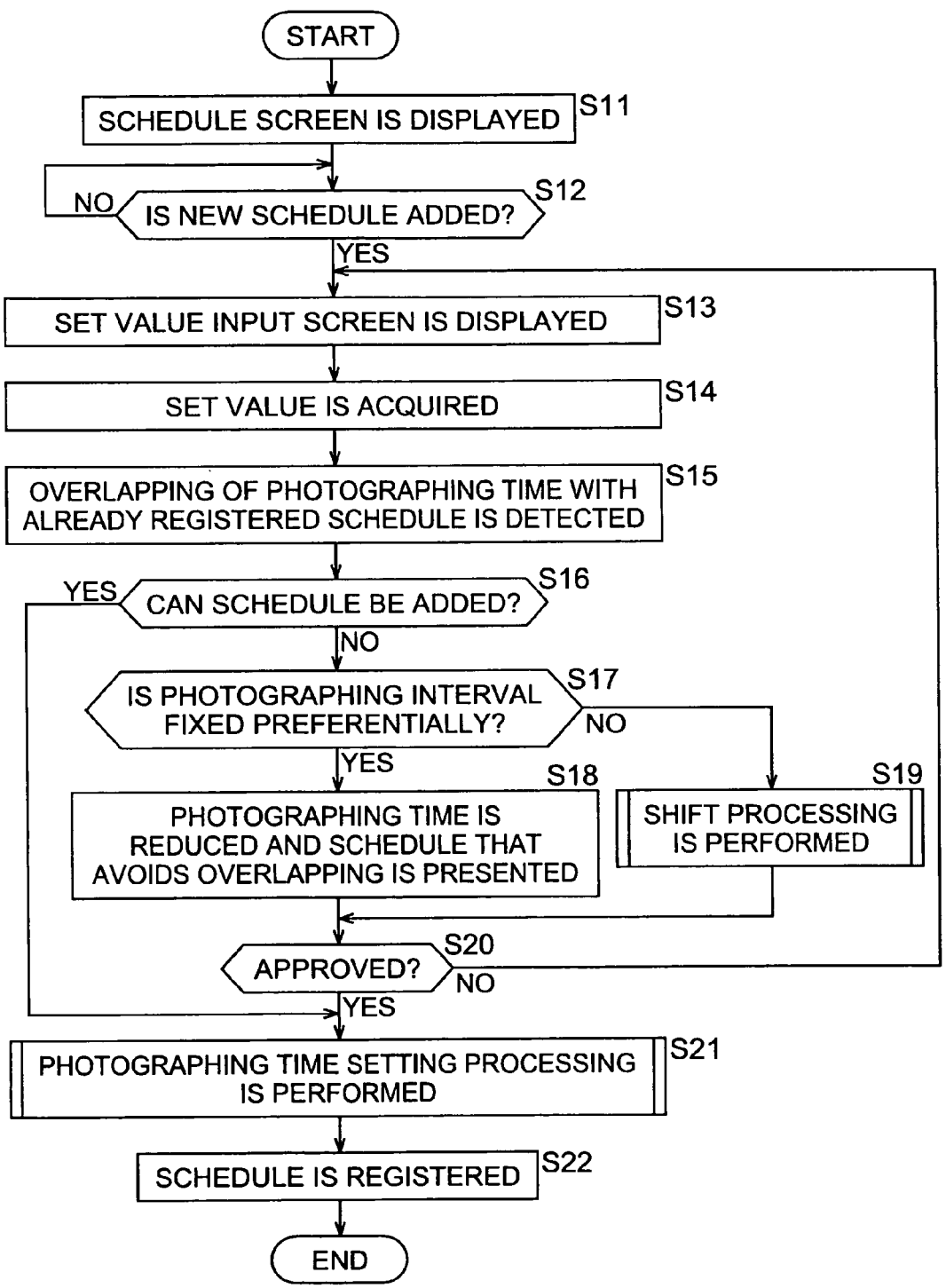
FIG. 14 is a flowchart illustrating the processing of setting a schedule.

FIG. 14 shows a flowchart illustrating the processing of setting a schedule that is performed by the control unit 44 shown in FIG. 5.

For example, the processing is started when the user operates the operation panel 23 shown in FIG. 1 and a sample that is an object of observation is selected. In step S11, the output unit 107 displays the schedule setting screen 120 (FIG. 6) on the operation panel 23 according to the control by the CPU 101.

After the processing of step S11, the processing advances to step S12, and the CPU 101 determines whether a new schedule will be added. For example, where the user operates the new schedule button 138 in the schedule setting screen 120, the input unit 106 acquires an operation signal corresponding to the user's operation and supplies the acquired operation signal to the CPU 101. The CPU 101 thereby determines that a new schedule will be added.

In step S12, the CPU 101 stops the processing till a new schedule is determined to be added, and in a case where the new schedule is determined to be added, the processing advances to step S13.

In step S13, the output unit 107 displays the set value input screen 160 (FIG. 7) on the operation panel 23 according to the control by the CPU 101, and the processing advances to step S14.

In step S14, the user inputs photographic conditions of the new schedule. Thus, a photographing interval of the new schedule is set by using the list boxes 161 and 162 of the set value input screen 160, a photographing time of the new schedule is set by using the combo box 163, and an photographing period of the new schedule is set by using the combo boxes 164 and 165. A time that constitutes 10% to 20% of the set value of the photographing interval that is a time lapse photography condition is set automatically as an allowed time and displayed in the combo box 166. Alternatively, manual input can be allowed within the range of the abovementioned time ratio and the user can input settings to the combo box 166.

Where the user thereafter operates the schedule addition button 123 shown in FIG. 6, the input unit 106 acquires the photographing interval, photographing time, and photographing period of the new schedule that have been set by the user and also the allowed time and supplies them to the CPU 101.

After the processing of step S14, the processing advances to step S15 and the CPU 101 performs the detection of overlapping of the photographing time of the already registered schedule that has been stored in the storage unit 108 and the photographing time of the new schedule that has been supplied from the input unit 106 in step S14 on the basis of photographic conditions that have been acquired in step S14, that is, on the basis of the photographing interval, photographing time, and photographing period of the new schedule that have been supplied from the input unit 106, and the processing advances to step S16.

In step S16, the CPU 101 determines whether the new schedule can be added. For example, where the photographing time of the already registered schedule and the photographing time of the new schedule have not been detected to overlap in step S15, the CPU 101 determines that the new schedule can be added, and where the photographing time of the already registered schedule and the photographing time of the new schedule have been detected to overlap, the CPU 101 determines that the new schedule cannot be added.

In a case where the CPU 101 determines in step S16 that the new schedule can be added, the processing advances to step S21, and in a case where the CPU 101 has determined that the new schedule cannot be added, the processing advances to step S17.

In step S17, the CPU 101 determines whether the settings are such as to fix the photographing interval preferentially for the new schedule, that is, determines whether the radio button 142 shown in FIG. 6 has been selected.

In a case where the CPU 101 determines in step S17 that the settings are such as to fix the photographing interval preferentially, the processing advances to step S18, and the CPU 101 avoids the overlapping of photographing time by reducing the photographing time. The output unit 107 displays on the operation panel 23 the schedule setting screen 120 (FIG. 9) that presents a schedule with a photographing time that has been changed as a result of avoiding the overlapping in response to the control by the CPU 101, and the processing advances to step S20.

In a case where the CPU 101 determines in step S17 that the settings are not such as to fix the photographing interval preferentially, the processing advances to step S19, the CPU 101 performs a shift processing by which the photographing time is caused to shift within the allowed time, and the processing advances to step S20. In the shift processing, for example, the schedule setting screen 120 (FIG. 10) in which the photographing time has been shifted within the allowed time range is displayed on the operation panel 23.

In step S20, the CPU 101 determines whether the user has approved the change presented in step S18 or S19.

For example, where the user operates the time change approval button 145 of the schedule setting screen 120 (FIG. 9) that has been displayed on the operation panel 23 in step S18 and the input unit 106 acquires the operation signal corresponding to this operation and supplies this signal to the CPU 101, the CPU 101 determines that the user has approved of the photographing time change. For example, where the user operates the approval button 147 of the schedule setting screen 120 (FIG. 10) that has been displayed on the operation panel 23 in the shift processing of step S19 and the input unit 106 acquires the operation signal corresponding to this operation and supplies this signal to the CPU 101, the CPU 101 determines that the user has approved the photographing time shift.

In a case where the CPU 101 determines in step S20 that the user has approved of the change presented in step S18 or S19, the processing advances to step S21.

In a case where the CPU 101 determines that the user has not approved of the change presented in step S18 or S19, the processing returns to step S13. The processing also returns to step S13 in a case where the overlapping has not been avoided even after the photographing time was shifted within the allowed time, as described hereinbelow, by the shift processing of step S19. Then, the set value input screen 160 (FIG. 7) is displayed again, and the user inputs again the set values and the same processing is thereafter repeated.

In step S21, the photographing time setting processing is executed by which the conditions such as photographic magnification and photographic point are inputted and the photographing time is set.

After the photographing time setting processing of step S21, the processing advances to step S22, and the CPU 101 stores and registers the new schedule (that is, photographic conditions acquired in step S14 or photographic conditions changed in step S18) in the storage unit 108. Further, for example, in a case where the photographing time of the already registered schedules has been shifted in the shift processing of step S19, the already registered schedule is re-registered (updated). The processing of setting the schedule is thereafter ended.

Figure 15:
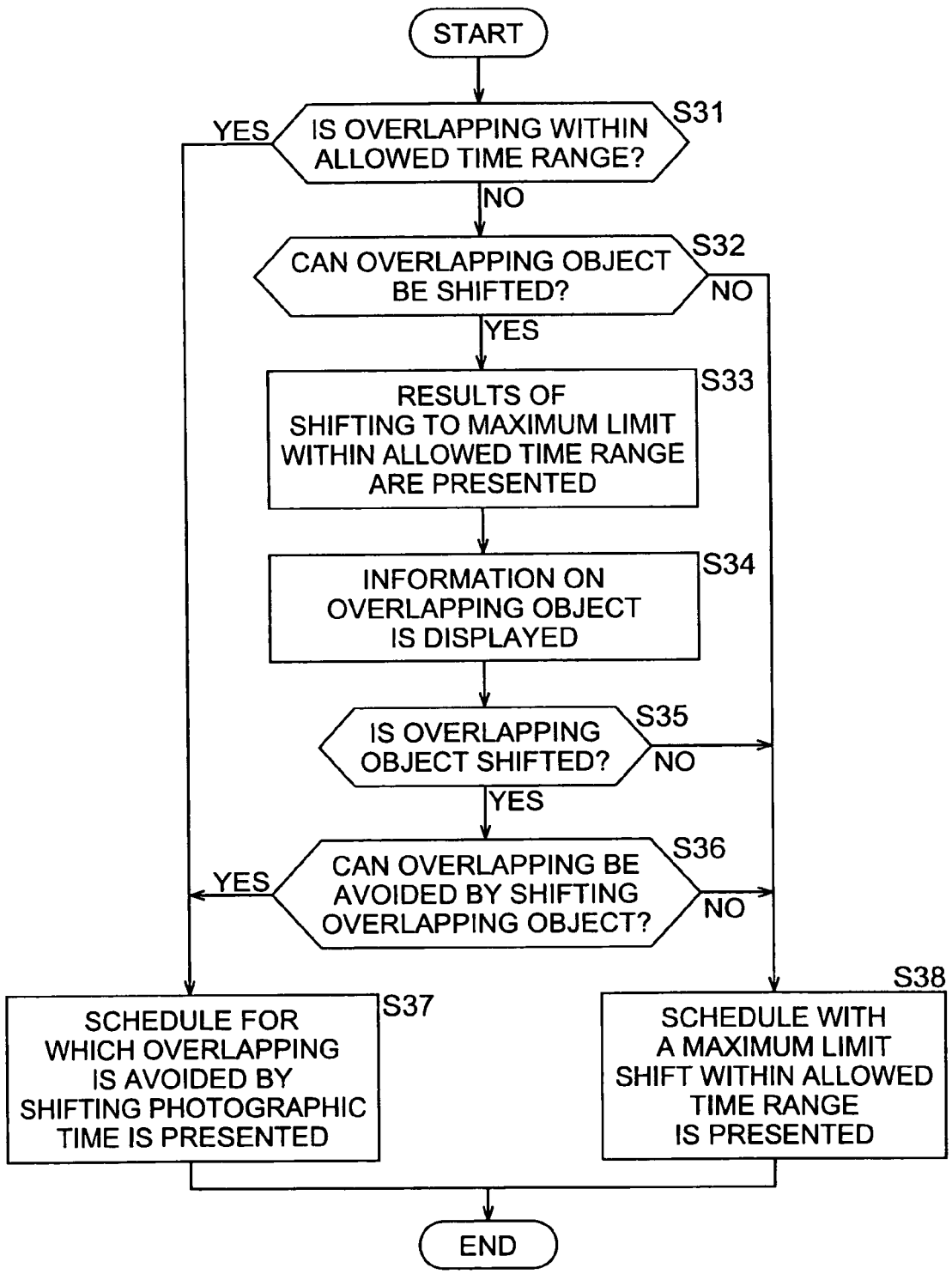
FIG. 15 is a flowchart illustrating a shift processing.

FIG. 15 is a flowchart illustrating the shift processing of step S19 shown in FIG. 14.

In Step S31, the CPU 101 determines whether the overlapping time of the photographing times that have been determined to overlap in step S15 shown in FIG. 14 is within the allowed time range acquired in step S14.

In a case where the CPU 101 determines in step S31 that the overlapping time is within the allowed time range, the processing advances to step S37, and in a case where the overlapping time is determined not be within the allowed time range, the processing advances to step S32.

In step S32, the CPU 101 confirms the schedule that is the overlapping object and determines whether the overlapping object can be shifted. For example, in a case where the preference order of the user for which the schedule that is the overlapping object has been registered is equal to or lower than the preference order of the user of the new schedule and the schedule that is the overlapping object is not set so that the photographing interval is fixed preferentially, the CPU 101 determines that the overlapping object can be shifted.

In a case where the preference order of the user for which the schedule that is the overlapping object has been registered is higher than the preference order of the user of the new schedule, or where the schedule that is the overlapping object is set so that the photographing interval is fixed preferentially, the CPU 101 determines that the overlapping object cannot be shifted. In other words, when the photographing times overlap, the schedule of the user with a lower preference order is changed.

In a case where the CPU 101 determines in step S32 that the overlapping object cannot be shifted, the processing advances to step S38, and in a case where it is determined that the overlapping object can be shifted, the processing advances to step S33.

In step S33, the CPU 101 shifts the overlapping photographing time within the allowed time range that has been set for the new schedule, that is, shifts the photographing time by a maximum time for which shifting is allowed, and displays the schedule setting screen that shows the shifting results. In this case, because the overlapping object can be shifted, the schedule setting screen 120 such as shown in FIG. 11 is displayed. If the user then operates the change button 148, the processing advances to step S34.

In step S34, the CPU 101 displays the information of the overlapping object on the operation panel 23 and displays a GUI that indicates that the overlapping object is shifted, and the processing advances to step S35. The user then confirms the information displayed on the operation panel 23, for example, the user that has registered the schedule that is the overlapping object and the allowed time that has been set for this schedule, and determines whether the overlapping object is to be shifted.

In step S35, the CPU 101 determines whether the overlapping object is to be shifted, that is, whether the user has determined that the overlapping object is to be shifted and has operated the GUI that indicates that the overlapping object is to be shifted.

In a case where the CPU 101 determines in step S35 that the overlapping object is not to be shifted, the processing advances to step S38, and in a case where it is determined that the overlapping object is to be shifted, the processing advances to step S36.

In step S36, the CPU 101 determines whether the overlapping of the photographing time of the new schedule and the photographing time of the already registered schedule has been avoided as a result of shifting the overlapping object. Where the overlapping is determined to be avoided, the processing advances to step S37, and where the overlapping is determined to be not avoided, the processing advances to step S38.

In step S37, the CPU 101 shifts the photographing time (either or both) for which overlapping has been detected and displays on the operation panel 23 the schedule setting screen that presents a schedule for which the overlapping has been avoided as a result of shifting. For example, in a case where the overlapping time is determined in step S31 to be within the allowed time, the schedule setting screen 120 with a shifted photographing time of the new schedule, such as shown in FIG. 10, is displayed. Further, for example, in a case where the overlapping is determined to have been avoided in step S36, a schedule setting screen is displayed in which both the photographing time of the new schedule and the photographing time of the already registered schedule have been shifted. The photographing time is shifted so as to obtain a minimum shift amount within the allowed time.

In step S38, the CPU 101 conducts maximum limit shifting of the photographing time for which overlapping has been detected within the allowed time, and displays on the operation panel 23 a schedule setting screen that presents the schedule obtained as a result of such shifting. For example, in a case is determined in step S32 that the overlapping object cannot be shifted, and in a case where it is determined in step S35 that the overlapping object is not to be shifted, the schedule setting screen is displayed in which the overlapping photographing time of the new schedule is shifted within the allowed time range that has been set for the new schedule. For example, in a case where it is determined in step S36 that the overlapping has not been avoided, a schedule setting screen is displayed in which the photographing time of both schedules is shifted within the allowed time range that has been set for the new schedule and within the allowed time that has been set for the already registered schedule.

The shift processing ends after the processing of steps S37 and S38.

The overlapping of photographing times can be avoided by shifting one or both of the photographing times that have been detected to overlap by such a shift processing. Further, even when the overlapping of photographing times cannot be avoided by shifting within the allowed time range, where the user is presented with a schedule in which the photographing times that have been detected to overlap are shifted to a maximum limit within the allowed time range, the user can use this schedule as a reference during resetting of photographic conditions and again input the set values of photographic conditions so as to avoid the overlapping.

Figure 16:
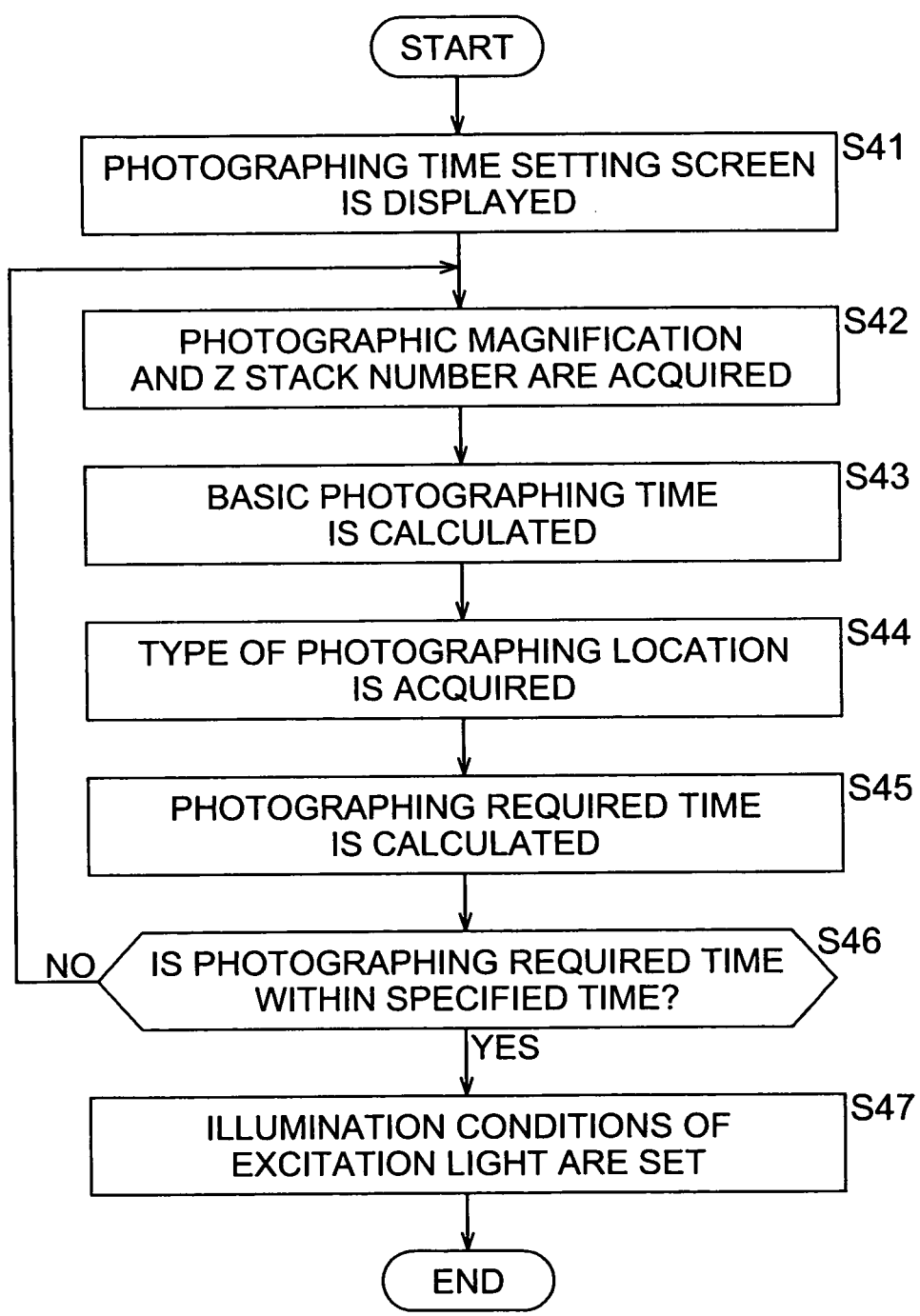
FIG. 16 is a flowchart illustrating the photographic condition setting processing.

FIG. 16 shows a flowchart explaining the photographing time setting processing of step S21 shown in FIG. 14.

In step S41, the output unit 107 displays the photographing time setting screen 170 (FIG. 12) on the operation panel 23 according to the control of CPU 101, and the processing advances to step S42.

Where the user selects the photographic magnification and Z stack number in step S42 by using the photographic magnification button 184 and radio button 85 of the photographing time setting screen 170, the input unit 106 acquires the photographic magnification and Z stack number selected by the user and supplies them to the CPU 101.

After the processing of step S42, the processing advances to step S43 and the CPU 101 calculates, on the basis of the photographic magnification and Z stack number supplied from the input unit 106 in step S42, the basic photographing time that is a time necessary to photograph the Z stack number at this photographic magnification, and the processing advances to step S44. For example, the basic photographing time can be found on the basis of a time required to switch the objective lens, an exposure time of the photographing element, and time required for movement in Z direction.

Where the user selects the type of photographic location in step S44 by using an observation location selection button 186 of the photographing time setting screen 170, the input unit 106 acquires the type of photographic location selected by the user and supplies it to the CPU 101.

After the processing of step S44, the processing advances to step S45, the CPU 101 calculates a required photographing time that is a total time necessary to photograph the number of photographic locations corresponding to the type of the photographic location supplied from the input unit 106 in step S42 within the basic time calculated in step S43, and the processing advances to step S46.

In step S46, the CPU 101 takes the photographing time that has been set by the user in the processing of setting the schedule shown in FIG. 14 as a specified time and determines whether the required photographing time calculated in step S45 is within the specified time.

In a case where the CPU 101 determines in step S46 that the required photographing time is not within the specified time, the processing returns to step S42 and then the same processing is repeated. Meanwhile, in a case where the CPU 101 determines in step S46 that the required photographing time is within the specified time, the processing advances to step S47.

Where in step S47 the user inputs illumination conditions of excitation light to an illumination condition display unit 183 of the photographing time setting screen 170 and operates a save button 174, the input unit 106 acquires the illumination conditions set by the user and supplies them to the CPU 101. The CPU 101 sets the illumination conditions so that the LED 48 for fluorescence can emit the excitation light under these illumination conditions, and the photographic condition setting processing is ended.

The overlapping of the photographing time of the new schedule and the photographing time of the already registered schedule is thus detected. Therefore, the new schedule can be registered so that the time lapse photography can be reliably performed. Further, in a case the photographing time of the new schedule and photographing time of the already registered schedule overlap, the changes of the photographing time and the like are presented to the user. Therefore, the user can easily change the schedule on the basis of these presentations.

Further, it is determined whether the required photographing time necessary for photographing based on the photographic conditions inputted by the user is within the specified time, and when the required photographing time is not within the specified time, the next processing, for example, setting of illumination conditions, is not performed. Therefore, the required photographing time can be reliably set within the specified time.

In a case where the required photographing time is not within the specified time, an alarm screen that informs the user that the specified time is exceeded is displayed and then the setting of photographic magnification or the like can be performed again. Furthermore, it can be presented to the user how to change the photographic conditions in order to fit the required photographing time within the specified time.

Further, the overlapping of photographing times of the schedules can be detected not only with the schedule that has already been registered by the user that registers the new schedule, but also with the schedule that has already been registered by another user, and matching with the control of schedules between the users can be performed.

The photographing start time of the time lapse photography can be set not only by using the set value input screen 160 shown in FIG. 7, but also, for example, by touching the time schedule display unit 121 of the schedule setting screen 120 shown in FIG. 6.

Further, each processing explained with reference to the above-described flowcharts is not necessarily performed in a time sequence according to the order described as the flowchart and can also include processing that is executed in parallel or individually (for example, parallel processing or object-based processing). Moreover, the program may involve processing with one CPU or discrete processing performed by a plurality of CPU.

The present invention is not limited to the above-described embodiments and various changes can be made without departing from the essence of the present invention.

What is claimed is:

1. A cell observation apparatus for observing a culturing process of cells according to an observation schedule designated by a user, the apparatus comprising:

a cell culture incubator with an operation control unit;

a photographic unit that photographs the cells according to the observation schedule;

at least one input unit within the control unit that acquires a new observation schedule in response to an input of photographic conditions by the user;

at least one CPU (Central Processing Unit) within the control unit that determines whether a photographing time of the photographic unit included in the photographic conditions of the new observation schedule that has been acquired by the at least one input unit overlaps a photographing time of the photographic unit included in the photographic conditions of an already registered observation schedule and changes the photographic conditions of either one or both of the observation schedules when the overlapping of the photographing times of the observation schedules has been determined by the at least one CPU;

a data storage unit within the control unit that registers the new observation schedule, or registers the new observation schedule and then re-registers the already registered observation schedule on the basis of the photographic conditions that are changed by the at least one CPU; and the cell culture incubator further comprises a stocker unit and a conveying unit.

2. The cell observation apparatus according to claim 1, wherein the photographic conditions of the observation schedule include at least a photographing frequency of the photographic unit in time-lapse photography, a photographing time, and a photographing interval;

the at least one CPU changes the photographic conditions of the observation schedule by shifting one or both of the photographing times, which have been determined to overlap by the at least one CPU, back or forth within an allowed time range that has been set for the respective observation schedule; and the storage unit registers the observation schedule in a case where the overlapping of photographing times of the observation schedules has been eliminated by changing the photographic conditions by the CPU.

3. The cell observation apparatus according to claim 2, wherein the allowed time, which is a time in which shifting of the photographing time by the at least one CPU is allowed, is determined by automatic computation of a predetermined ratio corresponding to the photographing interval or by manual input thereof.

4. The cell observation apparatus according to claim 2, further comprising:

an operation panel,
  wherein the operation panel displays an overlapping portion of the observation schedules after the change made by the at least one CPU, and in a case where the overlapping of photographing times of the observation schedules has not been eliminated despite the change in the photographic conditions of the observation schedule made by the least one CPU, the at least one input unit acquires a new observation schedule again in response to a change in the photographic conditions made by the user.

5. The cell observation apparatus according to claim 1, further comprising:

an operation panel,
  wherein the operation panel displays an overlapping state of the photographing times to the user when the photographing times have been determined to overlap by the at least one CPU, and the at least one CPU acquires a new observation schedule again in response to a change in the photographic conditions made by the user.

6. The cell observation apparatus according to claim 1, wherein;

a priority between a plurality of users is registered in the storage unit, the at least one CPU determines the priority between a plurality of users, and the at least one CPU changes the photographic conditions of an observation schedule of the user with a lower priority that has been registered in the storage unit by the at least one CPU when the observation schedules, for which the photographing times have been determined to overlap by the at least one CPU, have different users.

7. The cell observation apparatus according to claim 1, wherein the at least one CPU sets a time required for the photographic unit to photograph, so that photographing by the photographic unit is completed within the photographing time of a new observation schedule that has been acquired by the at least one input unit;

the at least one input unit acquires, in response to input by a user, a photographic magnification at which the cells are photographed and a Z stack number in a direction of an optical axis in which the cells are photographed;

the at least one CPU compounds a basic photographing time that is a time necessary to photograph the Z stack number that has been acquired by the at least one input unit at the photographic magnification acquired by the at least one input unit;

the at least one input unit acquires, in response to input by a user, the number of photographic points per plane perpendicular to an optical axis;

the at least one CPU computes a required photographing time that is a time required to photograph the number of photographic points that have been acquired by the at least one input unit, within the basic photographing time that has been calculated by the at least one CPU; and the at least one CPU determines whether the required photographing time calculated by the at least one CPU is within the photographing time of a new observation schedule that has been acquired by the storage unit, and wherein in a case where the required photographing time is determined by the at least one CPU not to be within the photographing time of a new observation schedule that has been acquired by the storage unit, either the acquisition of the photographic magnification and the Z stack number by the at least one input unit or the acquisition of the number of photographic points by the at least one input unit is conducted again.

8. A cell observation method for observing a culturing process of cells according to an observation schedule by which time lapse observations with a predetermined photographing time are performed at every predetermined photographing interval, the method comprising the steps of:

presenting to a user an observation schedule that has already been registered;

acquiring a photographing interval and a photographing time of a new observation schedule in response to an input of photographic conditions by the user;

determining whether photographing times of the new observation schedule and the already registered observation schedule overlap on the basis of the photographing interval and the photographing time; and changing, in a case where the photographing times have been determined to overlap, the photographic conditions of the observation schedule by shifting the photographing time of one or both of the observation schedules back or forth within an allowed time range that has been set in advance, and registering the observation schedule.

* * * * *